US011773765B2

(12) United States Patent
Bunjes

(10) Patent No.: US 11,773,765 B2
(45) Date of Patent: Oct. 3, 2023

(54) INTERNAL COMBUSTION ENGINE, COMBUSTION SYSTEMS, AND RELATED METHODS AND CONTROL METHODS AND SYSTEMS

(71) Applicant: Douglas David Bunjes, Saratoga Springs, UT (US)

(72) Inventor: Douglas David Bunjes, Saratoga Springs, UT (US)

(*) Notice: Subject to any disclaimer, the term of this patent is extended or adjusted under 35 U.S.C. 154(b) by 0 days.

(21) Appl. No.: 16/777,300

(22) Filed: Jan. 30, 2020

(65) Prior Publication Data

US 2020/0163617 A1 May 28, 2020

Related U.S. Application Data

(63) Continuation of application No. 16/538,527, filed on Aug. 12, 2019, which is a continuation of application
(Continued)

(51) Int. Cl.
*F02B 21/02* (2006.01)
*F02B 21/00* (2006.01)
(Continued)

(52) U.S. Cl.
CPC .............. *F02B 21/02* (2013.01); *A61B 3/14* (2013.01); *A61B 5/0071* (2013.01);
(Continued)

(58) Field of Classification Search
CPC . F02B 21/02; F02B 21/00; A61B 3/14; A61B 5/0071; A61B 5/4836;
(Continued)

(56) References Cited

U.S. PATENT DOCUMENTS

| 4,473,051 A | 9/1984 | Chorman |
| 4,915,084 A * | 4/1990 | Gonze .................. G01N 27/221 |
| | | 123/454 |

(Continued)

FOREIGN PATENT DOCUMENTS

| CA | 2699647 A1 | 10/2011 |
| CN | 103161562 A | 6/2013 |

(Continued)

OTHER PUBLICATIONS

Final Office Action for U.S. Appl. No. 15/540,359 dated Feb. 15, 2019.
(Continued)

*Primary Examiner* — Gonzalo Laguarda
(74) *Attorney, Agent, or Firm* — DORSEY & WHITNEY LLP

(57) ABSTRACT

Embodiments disclosed herein relate to internal combustion engines, combustion systems that include such internal combustion engines, and controls for controlling operation of the combustion engine. The internal combustion engine may include one or more mechanisms for injecting fuel, air, fuel-air mixture, or combinations thereof directly into one or more cylinders, and controls may operate or direct operation of such mechanisms.

17 Claims, 12 Drawing Sheets

Related U.S. Application Data

No. 15/540,359, filed as application No. PCT/US2015/067737 on Dec. 28, 2015, now Pat. No. 10,422,271.

(60) Provisional application No. 62/097,495, filed on Dec. 29, 2014, provisional application No. 62/097,506, filed on Dec. 29, 2014.

(51) Int. Cl.

| | | |
|---|---|---|
| A61B 3/14 | (2006.01) | |
| A61B 5/00 | (2006.01) | |
| A61K 41/00 | (2020.01) | |
| A61K 49/00 | (2006.01) | |
| A61K 49/22 | (2006.01) | |
| C07K 16/22 | (2006.01) | |
| F01L 9/14 | (2021.01) | |
| F01L 9/16 | (2021.01) | |
| F01L 9/20 | (2021.01) | |
| F02D 41/40 | (2006.01) | |
| F02B 75/02 | (2006.01) | |
| A61B 5/145 | (2006.01) | |
| A61B 5/1455 | (2006.01) | |
| A61N 1/40 | (2006.01) | |
| A61N 5/02 | (2006.01) | |
| A61N 5/06 | (2006.01) | |
| A61N 7/02 | (2006.01) | |
| F01L 9/10 | (2021.01) | |
| F02B 17/00 | (2006.01) | |
| F02B 23/10 | (2006.01) | |
| F02D 41/00 | (2006.01) | |
| F02M 25/10 | (2006.01) | |

(52) U.S. Cl.
CPC ........ *A61B 5/4836* (2013.01); *A61K 41/0028* (2013.01); *A61K 49/0004* (2013.01); *A61K 49/0034* (2013.01); *A61K 49/0043* (2013.01); *A61K 49/0093* (2013.01); *A61K 49/225* (2013.01); *C07K 16/22* (2013.01); *F01L 9/14* (2021.01); *F01L 9/16* (2021.01); *F01L 9/20* (2021.01); *F02B 21/00* (2013.01); *F02D 41/401* (2013.01); *F02D 41/402* (2013.01); *A61B 5/0095* (2013.01); *A61B 5/1455* (2013.01); *A61B 5/14532* (2013.01); *A61N 1/406* (2013.01); *A61N 5/025* (2013.01); *A61N 5/0625* (2013.01); *A61N 7/02* (2013.01); *F01L 9/10* (2021.01); *F02B 17/005* (2013.01); *F02B 23/104* (2013.01); *F02B 2075/025* (2013.01); *F02B 2275/14* (2013.01); *F02D 41/0027* (2013.01); *F02M 25/10* (2013.01)

(58) Field of Classification Search
CPC ............ A61K 41/0028; A61K 49/0004; A61K 49/0034; A61K 49/0043; A61K 49/0093; A61K 49/225; C07K 16/22; F01L 9/025; F01L 9/026; F01L 9/04; F02D 41/401; F02D 41/402

See application file for complete search history.

(56) References Cited

U.S. PATENT DOCUMENTS

| | | | |
|---|---|---|---|
| 5,179,926 A * | 1/1993 | Ament | ............... G01N 27/06 |
| | | | 123/494 |
| 6,223,846 B1 | 5/2001 | Schechter | |
| 6,314,948 B1 | 11/2001 | Cathcart et al. | |
| 6,810,546 B1 | 11/2004 | Smith et al. | |
| 7,050,900 B2 | 5/2006 | Miller et al. | |
| 8,613,269 B2 | 12/2013 | Shehter et al. | |
| 8,768,599 B2 * | 7/2014 | Blanchard | ............. F02D 29/02 |
| | | | 701/102 |
| 9,470,183 B2 | 10/2016 | Leone | |
| 10,422,271 B2 * | 9/2019 | Bunjes | ............ A61K 41/0028 |
| 2001/0002378 A1 | 5/2001 | Calandro | |
| 2001/0002379 A1 | 5/2001 | Schechter | |
| 2005/0182553 A1 | 8/2005 | Miller et al. | |
| 2010/0043753 A1 | 2/2010 | Gallagher et al. | |
| 2010/0147267 A1 * | 6/2010 | Kato | ................... F02M 59/44 |
| | | | 123/456 |
| 2011/0251743 A1 * | 10/2011 | Hu | ................... F02B 29/0443 |
| | | | 701/22 |
| 2012/0240909 A1 | 9/2012 | Geyer | |

FOREIGN PATENT DOCUMENTS

| | | |
|---|---|---|
| DE | 102011090142 A1 | 7/2013 |
| DE | 102012002566 A1 | 8/2013 |
| EP | 1736647 A1 | 12/2006 |
| GB | 2425808 A | 11/2006 |
| JP | H8072591 A | 3/1996 |
| JP | 200038940 A | 2/2000 |
| JP | 2001226457 A | 8/2001 |
| JP | 2005002932 A | 1/2005 |
| JP | 2005171794 A | 6/2005 |
| JP | 2006187743 A | 7/2006 |
| JP | 2006336502 A | 12/2006 |
| JP | 2007071037 A | 3/2007 |
| JP | 2007247508 A | 9/2007 |
| JP | 2008106653 A | 5/2008 |
| JP | 2008115786 A | 5/2008 |
| JP | 2008291847 A | 12/2008 |
| JP | 2009030487 A | 2/2009 |
| JP | 2010138772 A | 6/2010 |
| JP | 6419170 B2 | 10/2018 |
| WO | 2005042942 A1 | 5/2005 |

OTHER PUBLICATIONS

International Search Report and Written Opinion from International Application No. PCT/US2015/067737 dated Mar. 31, 2016.
Issue Notification for U.S. Appl. No. 15/540,359 dated Sep. 4, 2019.
Non-Final Office Action for U.S. Appl. No. 15/540,359 dated May 3, 2018.
Non-Final Office Action for U.S. Appl. No. 16/538,573 dated Sep. 3, 2019.
Notice of Allowance for U.S. Appl. No. 15/540,359 dated May 15, 2019.
U.S. Appl. No. 15/540,359, filed Jun. 28, 2017.
U.S. Appl. No. 16/538,527, filed Aug. 12, 2019.
U.S. Appl. No. 62/097,495, filed Dec. 29, 2014.
U.S. Appl. No. 62/097,506, filed Dec. 29, 2014.

* cited by examiner

INTERNAL COMBUSTION ENGINE, COMBUSTION SYSTEMS, AND RELATED METHODS AND CONTROL METHODS AND SYSTEMS

CROSS-REFERENCE TO RELATED APPLICATIONS

This application claims priority to U.S. patent application Ser. No. 16/538,573 filed on 12 Aug. 2019, which application claims priority to and is a continuation of U.S. patent application Ser. No. 15/540,359 filed on 28 Jun. 2017, which application is a National Stage Entry of PCT/US/2015/067737 filed on 28 Dec. 2015, which application claims priority to U.S. Provisional Application No. 62/097,495 filed on 29 Dec. 2014 and U.S. Provisional Application No. 62/097,506 filed on 29 Dec. 2014, the disclosures of which are incorporated herein, in their entirety, by this reference.

BACKGROUND

This disclosure relates to an internal combustion engine that may operate on gaseous fuel, liquid fuel, solid fuel, or combinations thereof.

Generally, internal combustion engines may have any number of configurations and sizes. For instance, an internal combustion engine may have various piston layouts, such as in-line, flat (also known as boxer), and V configurations. Also, an internal combustion engine may have a rotary configuration. Improving construction and/or operation of the internal combustion engine may lead to improved or more efficient operation, improved useful life, reduced operating costs, etc.

Accordingly, users and manufacturers of internal combustion engines continue to seek improvements thereof.

SUMMARY

Embodiments described herein are directed to an internal combustion engine that includes at least one combustion chamber, output shaft, and energy conversion mechanism for converting the energy produced during combustion of a fuel into mechanical output at the output shaft (e.g., converting pressure increase in the combustion chamber into rotation of the output shaft). In an embodiment, the fuel and oxidizer are injected into the combustion chamber and a combustion reaction produces a pressure increase therein; the engine may include one or more energy conversion mechanisms configured to convert the increased pressure in the combustion chamber into mechanical energy, such as rotation of the output shaft.

At least one embodiment includes a combustion engine that has an output shaft and one or more combustion chambers. Furthermore, such combustion engine includes one or more conversion mechanisms each located in corresponding ones of the one or more combustion chambers. The one or more conversion mechanisms are configured to convert a pressure increase in the combustion chamber into rotation of the output shaft. Such combustion engine also includes one or more fuel injectors operably connected to a supply of fuel and configured to inject the fuel directly into the combustion chamber. Additionally, such combustion engine includes one or more oxidizer injectors operably connected to a supply of an oxidizer and configured to inject the oxidizer into the combustion chamber.

This disclosure also involves a combustion engine according to one or more additional or alternative embodiments. Such combustion engine includes an engine block including one or more cylinders therein. Such combustion engine also includes a crankshaft rotatably secured to the engine block and one or more pistons movably positioned in the one or more cylinders and operably connected to the crankshaft. Moreover, such combustion engine includes one or more fuel injection ports unobstructedly opening into corresponding ones of the one or more cylinders, and one or more oxidizer injection ports unobstructedly opening into corresponding ones of the one or more cylinders. Such combustion engine further includes one or more oxidizer injectors positioned in corresponding ones of the one or more oxidizer injection ports and configured to inject an oxidizer into the corresponding one or more cylinders.

At least one embodiment involves a controller for operating an internal combustion engine that includes one or more combustion chambers and an output shaft rotatable in response to combustion of fuel in the combustion chambers. The controller includes a processor and a memory coupled to the processor and containing computer-executable instructions. Furthermore, execution of the computer-executable instructions by the processor causes the controller to perform the acts of receiving one or more operation inputs related to an operating parameter of the internal combustion engine and receiving one or more inputs from one or more sensors. In addition, execution of the computer-executable instructions by the processor causes the controller to perform the acts of determining the amount of air to inject into the one or more combustion chambers of the internal combustion engine and operating one or more air injectors to directly inject air into the one or more combustion chambers of the internal combustion engine.

Embodiments also include a computer controlled internal combustion engine system that includes an internal combustion engine and controller. The internal combustion engine includes an output shaft, one or more combustion chambers, and an energy conversion mechanism configured to convert a pressure increase in the one or more combustion chambers into rotation of the output shaft. The internal combustion engine also includes one or more air injectors operably connected to corresponding ones of the one or more combustion chambers, mechanically decoupled from the output shaft, and configured to unobstructedly inject air into the one or more combustion chambers. The controller is operably coupled to the one or more air injectors. Moreover, the controller is configured to receive one or more operation inputs related to an operating parameter of the internal combustion engine and to receive one or more inputs from one or more sensors. The controller is also configured to determine the amount of air to inject into one or more combustion chambers of the internal combustion engine and to operate one or more air injectors to directly inject air into the one or more combustion chambers of the internal combustion engine.

One or more embodiments include a method of operating an internal combustion engine. The method includes receiving one or more operation inputs related to an operating parameter of the internal combustion engine and receiving one or more inputs from one or more sensors. The method also includes determining the amount of air to inject into one or more combustion chambers of the internal combustion engine and injecting a selected and/or predetermined amount of air into the one or more combustion chambers of the internal combustion engine by operating one or more air injectors operably connected to the one or more combustion chambers. The method further includes injecting a selected and/or predetermined amount of fuel into the one or more combustion chambers of the internal combustion engine and combusting the fuel in the one or more combustion chambers, thereby rotating an output shaft of the internal combustion engine.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments, wherein identical reference numerals refer to identical or similar elements or features in different views or embodiments shown in the drawings.

DETAILED DESCRIPTION

Figure 1:
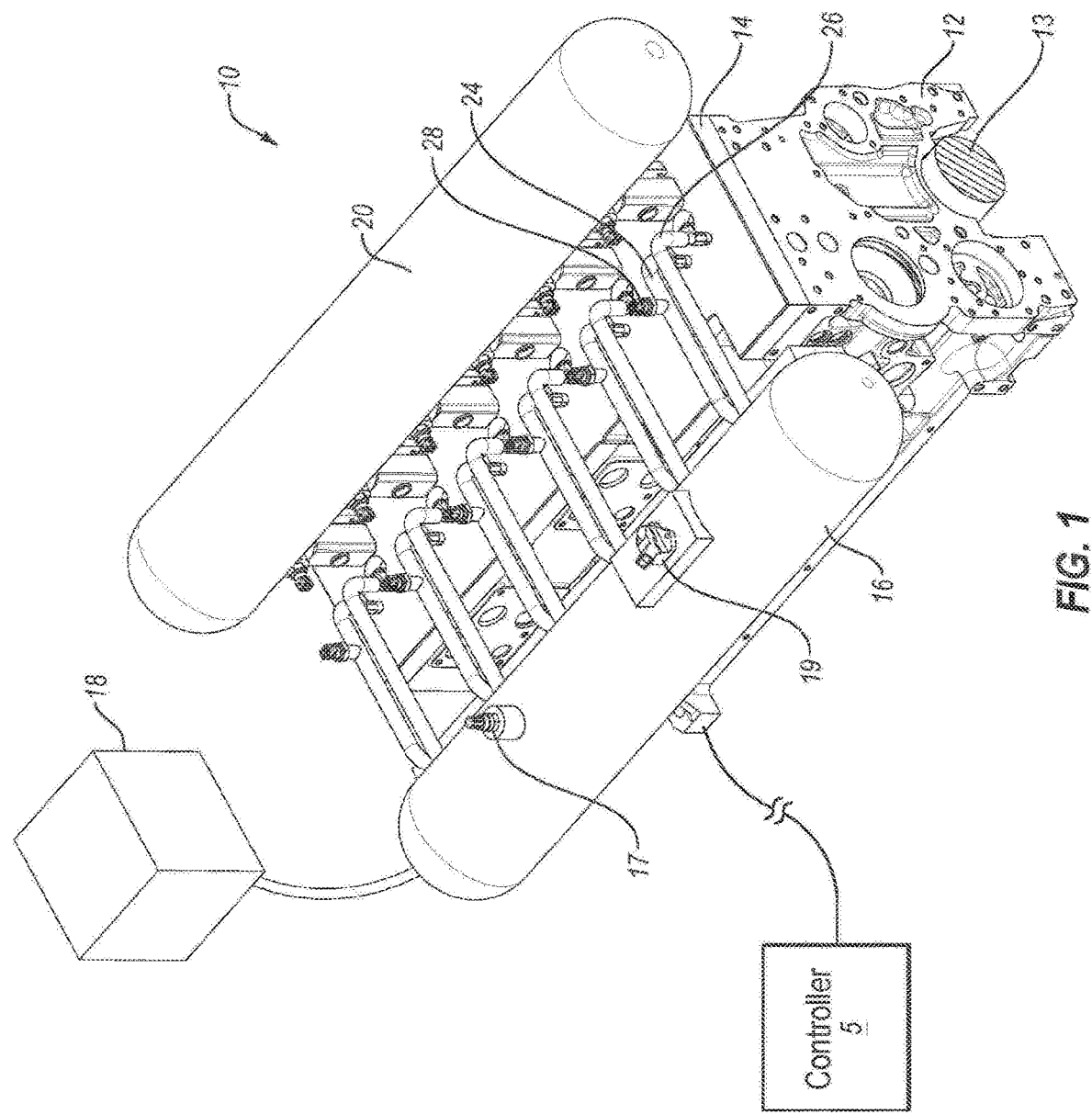
FIG. 1 is a front isometric view of an internal combustion engine according to an embodiment.

Embodiments described herein are directed to an internal combustion engine that includes at least one combustion chamber, output shaft, and energy conversion mechanism for converting the energy produced during combustion of a fuel into mechanical output at the output shaft (e.g., converting pressure increase in the combustion chamber into rotation of the output shaft). In an embodiment, the fuel and oxidizer are injected into the combustion chamber and a combustion reaction produces a pressure increase therein; the engine may include one or more energy conversion mechanisms configured to convert the increased pressure in the combustion chamber into mechanical energy, such as rotation of the output shaft.

Generally, the combustion chamber and/or the energy conversion mechanism may vary from one embodiment to the next. For instance, the internal combustion engine may include one or more cylinders and corresponding pistons that may define or form the combustion chamber thereof. The energy conversion mechanism may include the pistons movable in the cylinders in response to combustion of a fuel and air mixture. The pistons may be rotatably mounted on the output shaft (e.g., on a crankshaft), such that linear/reciprocating movement thereof (e.g., in a two- or four-stroke cycle) may be converted to rotation of the crankshaft. Alternatively or additionally, the engine may include a linear output mechanism that may be moved linearly and/or may reciprocate in response to combustion and/or pressure increase in the combustion chamber.

Additionally or alternatively, the internal combustion engine may be a rotary engine (e.g., Wankel engine, etc.) and may include a combustion chamber at least in part formed or defined non-reciprocating mechanism(s) that may convert the energy produced during combustion into rotation of the output shaft. For example, the combustion chamber of the engine may be formed or defined by and between rotor and housing (e.g., for a Wankel engine). Hence, for instance, the energy conversion mechanism may include a rotor that may rotate an output shaft in response to a pressure increase produced in the housing during and/or after combustion of fuel.

In some instances, in a four-stroke cycle of a reciprocating internal combustion engine that includes one or more pistons, air and fuel may be enter an upper end of the cylinder by the descending piston and may be compressed as the pistons rise during their upward stroke. The mixture is ignited and combusted in the cylinder, which forces the pistons to commence their next downward stroke. The final upward stroke expels the gases resulting from combustion, and thereafter the next suction stroke commences. Generally, air enters the combustion chamber of the engine through one or more intake valves that may open during the down stroke of the piston. Furthermore, the fuel is delivered into the cylinder, and after the intake valves close, the cycle above-described commences.

In a conventional engine, each cylinder may have at least one fuel-air intake port controlled by an intake valve and at least one exhaust port for exhaust gas, which also may be controlled by an exhaust valve. Some conventional engines may have two or more intake valves and/or two or more exhaust valves. Generally, the intake and/or exhaust valves may be opened and closed at precise times during the engine's cycle, which may involve complex timing connections (e.g., belts, chains, etc.) and cams that may actuate the intake and/or exhaust valves. For example, a timing belt may connect engine's crankshaft to a cam shaft that may open and close intake and/or exhaust valves based on the rotation of the crankshaft and positions of pistons in corresponding cylinders (i.e., timing the piston positions to the intake and exhaust valve openings and closings). Some conventional engines may include electronically controlled and/or operated intake and/or exhaust valves.

In some instances, a conventional engine may have a Gasoline Direct Injection (GDI) system in which a fuel injector may feed fuel directly into the cylinder. Conventional engines with the GDI systems may include intake valves (e.g., poppet or stem valves), which may open for air intake, and exhaust valves, which may open for gas exhaust. Hence, such engines may have a timing mechanism and a cam shaft to time opening and closing of the intake and exhaust valves during the engine's cycle.

Generally, as mentioned above, the internal combustion engine according to one or more embodiments described herein includes one or more combustion chambers (e.g., the internal combustion engine may have one or more cylinders that may include combustion chambers and may be arranged in any suitable manner and may have any suitable size). In an embodiment, the combustion system includes one or more mechanisms for injecting fuel, air, fuel-air mixture, or combinations thereof into one or more combustion chambers of the internal combustion engine (e.g., into cylinders, combustion chamber(s) of a rotary engine, such a Wankel engine, etc.). Additionally, in some examples, quantities of the injected fuel, air, fuel-air mixture, or combinations thereof may by accurately measured and/or controlled as well as adjusted during operation of the internal combustion engine. While references herein are made generally to "air," it should be appreciated that any suitable oxidant may be mixed with fuel and/or injected into the cylinders (e.g., oxygen ($O_2$)).

Moreover, in some embodiments, reducing moving parts in the internal combustion engine (as compared with a conventional combustion engine) may reduce mechanical losses during operation (e.g., losses resulting from friction of various components), reduce the weight of the internal combustion engine, and/or otherwise improve efficiency thereof. Additionally or alternatively, in at least one embodiment, the internal combustion engine may be simpler or less expensive to fabricate and/or maintain during operation.

In an embodiment, the internal combustion engine includes one or more fuel injectors to inject fuel directly into the combustion chamber(s) (e.g., into the cylinders). Moreover, in some embodiments, the internal combustion engine includes one or more air injectors that may inject air directly into the combustion chamber(s) (e.g., into the cylinders of the internal combustion engine). For example, in contrast to the conventional engine, the internal combustion engine described herein may have no intake valves for opening and/or closing air flow into the combustion chamber(s).

According to one or more embodiments, air injectors may be operated independently of the state of the combustion chamber (e.g., independent of piston positions and/or rotation of the crankshaft). For example, during some portions of the combustion cycle, the internal combustion engine may compress fuel and/or air in the combustion chamber (e.g., during an upstroke of the pistons). In other words, the air, fuel, fuel-air mixture may be injected into the combustion chamber at any time during the combustion cycle (e.g., when the piston is located at any suitable position in the cylinder).

In an embodiment, the internal combustion engine includes one or more exhaust ports for exhausting combusted gasses from the combustion chamber. Under some operating conditions, the exhaust ports may operate independently of the rotation of the output shaft (e.g., independent of the rotation of the crankshaft and/or reciprocation of piston location in the cylinder(s)). For example, one, some, or each of the cylinders may include a dedicated exhaust port, and an exhaust valve (e.g., electromechanical valve) may control the flow of exhaust gases from the corresponding cylinder(s) through the exhaust port(s).

In at least one example, one, some, or each of the cylinders of the internal combustion engine include a fuel injection port, an air injection port, and an exhaust port, each of which is in fluid communication with the respective cylinders. More specifically, fuel may be injected into the cylinder through the fuel injection port, air may be injected into the cylinder through the air injection port, and exhaust gas may exit the cylinder through the exhaust port. As mentioned above, valves controlling fuel injection, air injection, and gas exhaust at corresponding ports may operate independently of one another. Furthermore, the amount of air and/or fuel injected into the combustion chamber may be determined and/or preset prior to injection thereof.

For instance, the one or more valves or injectors at the air injection ports may open for a selected (e.g., calculated) and/or predetermined amount of time to inject a selected (e.g., calculated) and/or predetermined amount of air into the cylinder (e.g., the valves may be electrically or electromagnetically operated, hydraulically operated, etc.). In some embodiments, one, some, or all of the cylinders of the internal combustion engine may have multiple fuel injection ports, multiple air injection ports, multiple exhaust ports, or combinations thereof.

As mentioned above in some embodiments, the internal combustion engine includes reciprocating pistons that reciprocate in the corresponding cylinders during the combustion cycle. Generally, reciprocating movement of the pistons in the cylinders may produce rotation of the crankshaft. Hence, number of rotations per minute (RPM) of the crankshaft may be proportionate to the number of reciprocations of pistons or cycles in one, some, or all of the cylinders of the engine. In a conventional engine, opening and/or closing of spring-loaded valves may limit the frequency of piston's cycles in a cylinder (e.g., as the frequency of valve openings increases, the springs closing the valves may be unable to close the valve in a suitable amount of time and/or the valves may become unseated); this may in turn limit the operating range of RPM for the conventional engine. By contrast, however, it should be appreciated that the internal combustion engine described herein may operate at any suitable range of RPM. For instance, direct injection of air into the cylinders (and absence of the valves and springs) in the internal combustion engine may facilitate operation of the engine at higher RPM (as compared with a conventional engine (e.g., with similar number of cylinders and/or displacement)).

FIG. 1 is a front isometric view of an internal combustion engine 10 according to an embodiment. In the illustrated embodiment, the engine 10 includes a block 12 that has six in-line cylinders arranged in a straight line, which at least partially define combustion chambers of the engine 10. It should be appreciated, however, that the engine may have any number of cylinders and any number of suitable cylinder arrangements, as discussed above (e.g., V, rotary, boxer, etc.).

As described above, the engine 10, generally, includes combustion chamber, a mechanism for combusting the fuel therein, and a mechanism for converting the energy produced during combustion into a mechanical energy (e.g., rotation of an output shaft). For instance, while the combustion chambers of the engine 10 are defined by cylinders and corresponding pistons, it should be also appreciated that the engine may have any number of suitably configured combustion chambers. In some embodiments, the engine may have multiple pistons (e.g., two, three, etc.) driven from and/or operating in a single cylinder, which collectively may define a combustion chamber. Moreover, as noted above, in one or more embodiments, the engine may be a non-reciprocating and/or pistonless engine and may convert pressure produced during combustion directly into rotating motion (e.g., wave disk engine, Wankel engine, etc.).

As mentioned above, the engine may include an output shaft. For example, the engine 10 includes a crankshaft 13 that may be rotatably positioned in and/or secured to the block 12. Furthermore, as described in more detail below, in some embodiments, pistons reciprocate in the corresponding cylinders to produce rotation of the crankshaft 13. In some examples, the pistons are rotatably connected to the crankshaft 13, and reciprocation thereof produces corresponding rotation of the crankshaft 13. Generally, the crankshaft 13 may be connected to any number of suitable devices or systems and may provide rotational power thereto.

In an embodiment, reciprocating movement of the pistons in the cylinders is generated from combustion of fuel and an oxidant (e.g., air) in the cylinder. For instance, the cylinders are at least partially sealed during the combustion and the pressure produced from the combustion exerts force onto the corresponding pistons, thereby producing linear and reciprocating movement thereof (as described above). For example, the engine 10 includes a cylinder head 14 connected to or integrated with the block 12, and the cylinder head 14 and block 12, collectively, seal or close the cylinders in a manner that may form substantially pressure tight environment during combustion of fuel and air in the cylinders.

In some examples, to facilitate sealing between the block 12 and the cylinder head 14, a head gasket may be positioned therebetween. It should be appreciated, however, that the engine may have any number of suitable configurations and, in some instances, may not require a head gasket. For instance, the block 12 and cylinder head 14 may be integrally formed.

As described above, air, fuel, fuel-air mixture, or combinations thereof may be injected directly into one or more of the cylinders. For example, the engine 10 includes fuel lines 24 operably connected with the corresponding cylinders, such that fuel may be injected through the fuel line and directly into the cylinders. It should be appreciated that one, some, or all of the cylinders may include any suitable number of fuel lines operably connected thereto.

In an embodiment, the engine 10 includes a fuel sensor 28 (e.g., octane sensor). In at least one example, the fuel sensor 28 is operably connected to the fuel lines 24 to detect the type of fuel therein. Accordingly, for example, the engine may receive any suitable fuel (e.g., any fuel that may be detected and/or identified by the sensor 28 For example, the fuel sensor 28 may differentiate among gasoline (petrol), ethanol, diesel, liquefied natural gas (LNG), liquefied petroleum gas (LPG), hydrogen, etc. It should be appreciated that the one, some, or all of the fuel lines 24 may include a separate fuel sensor 28. In an embodiment, the fuel sensor 28 may be configured to detect the amount of ethanol in gasoline and/or in a similar type of fuel.

In some embodiments, as described below in more detail, the engine 10 includes a control mechanism for regulating the flow or injection of fuel from the fuel lines 24 into the corresponding cylinders. For example, the engine may include valves, fuel injectors, etc., which may be positioned between the fuel line 24 and the cylinder (e.g., the fuel lines 24 may connect to corresponding fuel injectors that may regulate supply and/or injection of fuel into such cylinders).

In some embodiments, the engine 10 includes air lines 26 operably connected to the corresponding cylinders. It should be appreciated that one, some, or all of cylinders may include one or more air lines operably connected thereto. The air lines 26 may supply one or more oxidants into the cylinders of the engine 10. As described below, the engine may include one or more mechanisms for controlling the flow or supply of the oxidants from the air lines 26 into the cylinders (e.g., valves, air injectors, etc.). Generally, any number of suitable oxidants, such as air, may be injected directly into the cylinder(s). For example, similar to the fuel injectors, a valve or an air injector may be positioned between the air lines 26 and the cylinder and may regulate supply or injection of air into the cylinder (e.g., air lines 26 may be operably connected to corresponding air injectors, which may regulate air flow from the air lines 26 into the cylinder(s)).

In an embodiment, the air lines 26 connect to an air intake manifold 16 and may receive air therefrom. It should be appreciated that one, some, or all of the air lines may be connected to the air intake manifold 16 and may receive air therefrom. Alternatively, one or more of the air lines may be connected to any number of suitable sources of oxidant (e.g., directly connected to a compressor, to a reservoir tank or accumulator, etc.). In any event, the air lines 26 may supply air into the cylinders of the engine 10.

As described below in more detail, the intake manifold 16 may distribute air to the various air lines 26 connected thereto (e.g., the air in the intake manifold 16 may be compressed). In other words, in at least one embodiment, the air lines 26 may be connected to a source of compressed air. It should be appreciated, however, that a particular source of compressed air to the air lines 26 may vary from one embodiment to the next (e.g., the source of compressed air may include a compressed air tank).

Generally, the intake manifold 16 forms an enclosure that is configured to contain and distribute air to the air lines 26. In some embodiments, the intake manifold 16 has a generally tubular, cylindrical shape with closed ends. It should be appreciated, however, that the intake manifold may have any number of suitable shapes and/or sizes (e.g., rectangular cross-sectional shape, etc.). In any event, air may be supplied into the intake manifold 16 and may be further distributed thereby to the air lines 26 connected thereto.

In some embodiments, a compressor 18 is operably connected to the intake manifold 16 to supply air (e.g., compressed air) thereto, which may be further distributed through the air lines 26 into the cylinders. Generally, the compressor 18 may be any suitable compressor that may operate independent of operation of the engine 10 (e.g., the compressor 18 may be electrically powered. Additionally or alternatively, the compressor 18 may be at least in part driven or operated by or from the rotation of the crankshaft 13. In any event, compressor 18 may compress air and may supply the compressed air to the intake manifold 16.

In some embodiments, the engine may include one or more cylinders configured and/or dedicated for compressing air that may be supplied to the air lines 26, intake manifold 16, air injectors (described below in more detail), or combinations of the foregoing. For example, the engine may include one or more cylinders in fluid communication with outside environment and in fluid communication with the air lines 26, intake manifold 16, air injectors (described below in more detail), or combinations of the foregoing. Corresponding one or more pistons may move or reciprocate in the cylinders to intake and compress the air therein. For example, the internal space of the cylinder may be substantially sealed until a suitable pressure is reached and, subsequently, one or more valves may open to allow the compressed air to flow into and/or toward the air lines 26, intake manifold 16, air injectors (described below in more detail), or combinations of the foregoing. In an embodiment, the pistons may be connected to the crankshaft in a similar manner as the power pistons of the engine (e.g., pistons that rotate the crankshaft, as described below). In other words, in some embodiments, a compressor may be integrated with the engine.

In one or more examples, the engine may include one or more filters, which may improve quality of the air supplied into the cylinders. For instance, a HEPA filter, a water separation filter, etc., may be placed between the compressor 18 and the cylinders of the engine (e.g., between the compressor 18 and the intake manifold 16). Such filter(s) may remove particles and/or liquids from the air entering the manifold 16 and/or cylinders of the engine.

The engine according to at least one embodiment may include a temperature sensor that may determine or measure the temperature of air before injection thereof into the cylinder. For example, the engine 10 includes a temperature sensor 17 that may sense temperature of the air in the intake manifold 16. In the illustrated embodiment, the engine 10 includes a pressure sensor 19 (e.g., a manifold absolute pressure sensor (MAP)). For example, a controller 5 may operate the air injectors (described below) in a manner that injects a selected (e.g., calculated) and/or predetermined amount of air into the cylinder at least in part based on the readings from the pressure sensor 19 and/or temperature sensor 17. It should be appreciated, however, that one or more sensor functions may be included within a single sensor and/or one or more sensors may be included within a single enclosure. Moreover, in some embodiments, the engine may include one or more different sensors or no sensors (e.g., such as to be manually and/or electromechanically operated).

Generally, as mentioned above, after combustion of fuel in the engine's combustion chamber, the produced gas is expelled from the combustion chamber (e.g., to allow additional fuel and air to enter the chamber). For example, piston movement in the cylinder may expel the exhaust gas from the cylinder through one or more connections and into the exhaust manifold 20. Hence, for example, the engine 10 includes exhaust connections. More specifically, in an embodiment, the engine 10 includes an exhaust manifold 20 operably connected to the cylinders, such that the exhaust gas from the cylinders may enter the exhaust manifold 20.

As described below in more detail, the engine according to one or more embodiments may include one or more exhaust valves that may control the flow of exhaust gas from the cylinders into the exhaust manifold. Moreover, generally, the exhaust manifold may be similar to the intake manifold. For example, the exhaust manifold 20 has a tubular shape and capped ends, which may be similar to a gas cylinder. It should be appreciated, however, that the exhaust manifold may have any suitable shape and/or size.

Figure 2:
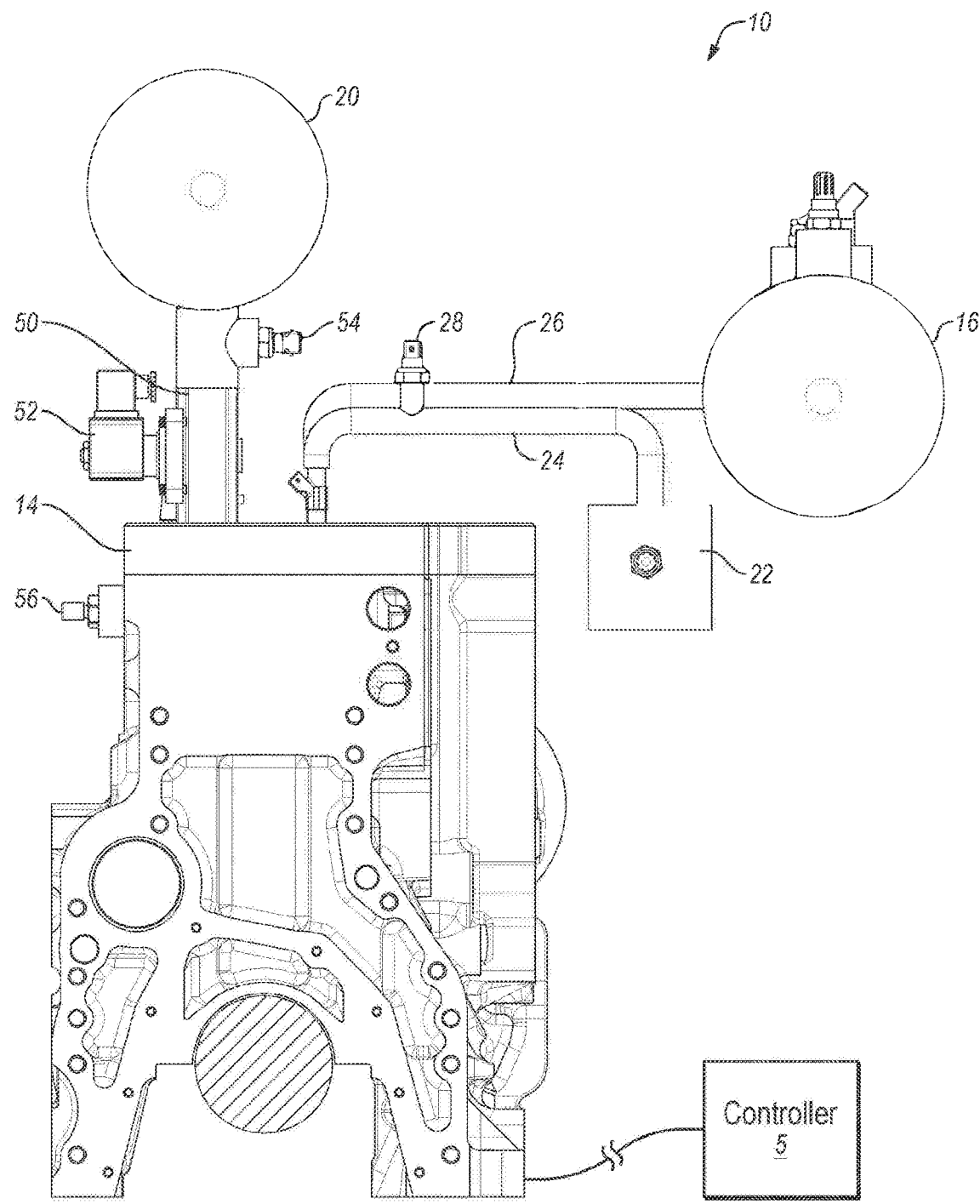
FIG. 2 is a side view of the internal combustion engine of FIG. 1.
Figure 3:
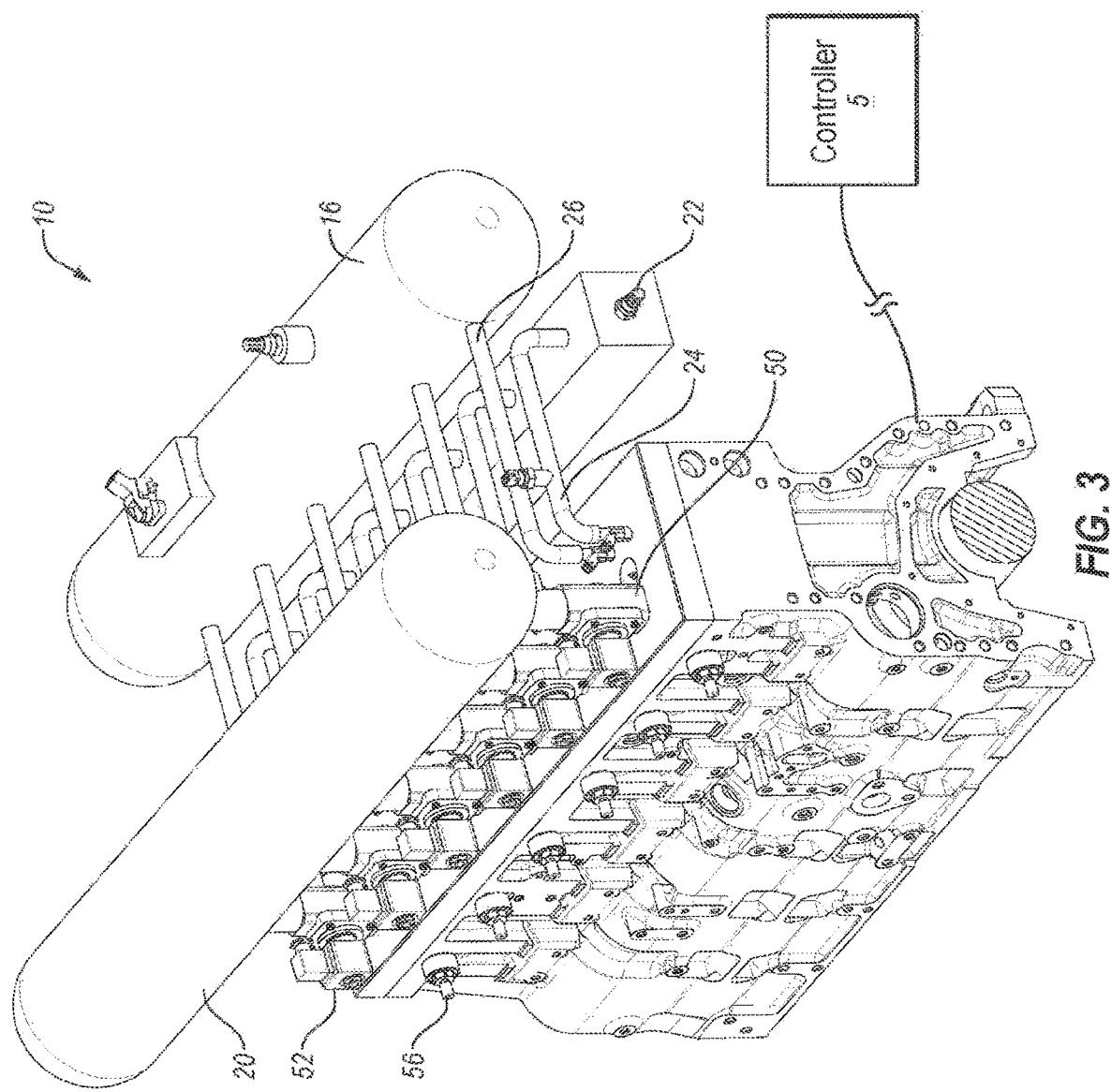
FIG. 3 is a back isometric view of the internal combustion engine of FIG. 1.

FIGS. 2-3 illustrate respective side view and back isometric view of the engine 10 according to an embodiment. In the illustrated embodiment, exhaust lines 50 connect the exhaust manifold 20 to the cylinders of the engine 10. It should be appreciated, however, that in some examples, the exhaust gas may exit one, some, or all of the cylinders in any number of suitable ways (e.g., without entering the exhaust lines and/or exhaust manifold). In one or more embodiments, the engine may have any number of suitable exhaust systems in addition to and/or in lieu of the exhaust described herein.

In the illustrated embodiment, the engine 10 includes exhaust valves 52 operably connected to the corresponding exhaust lines 50 to control outflow of exhaust gas from the cylinders. For example, the exhaust valves 52 may be positioned on the corresponding exhaust lines 52 and may allow and restrict gas flow therethrough. Additionally or alternatively, one, some, or all of the exhaust valves may be positioned between the exhaust lines 50 and the cylinders (e.g., exhaust valves may be positioned inside cylinder(s), just outside the cylinder(s), or otherwise between the exhaust lines 50 and the cylinders and/or the cylinder head 14).

Generally, to control the outflow of the exhaust gasses, the exhaust valves 52 may be operated between fully open position (e.g., least restrictive or unrestricted outflow through the exhaust lines 50) and fully closed position (e.g., substantially or completely restricted outflow through the exhaust lines 50). Moreover, the exhaust valves 52 may be operated to restrict outflow from the cylinders at any number of partially restricted positions between the fully open and fully closed positions. In any event, exhaust gas flow from one, some, or each of the cylinders into the exhaust manifold 20 may be controlled by a corresponding exhaust valve 52 that may be electrically or electromechanically actuated, hydraulically actuated, pneumatically actuated, etc., to allow exhaust gas to flow out of the cylinders (e.g., into the exhaust manifold 20). In an example, the exhaust valves 52 may be actuated from the controller 5. Hence, the timing of the opening and/or closing of the exhaust valves 52 may be electronically controlled and may be based on any number of suitable parameters or inputs.

When the exhaust valves 52 are closed, the corresponding cylinders may be substantially sealed, such that combustion of the fuel may produce pressure therein and may exert force onto and move the pistons, thereby rotating the crankshaft and generating mechanical output of the engine 10. The exhaust valves 52 may be selectively opened to allow the exhaust gas to exit the cylinder during and/or after combustion. Moreover, in some embodiments, negative pressure or partial vacuum may be created in the exhaust manifold 50 to assist with removal of the exhaust gas from the cylinder(s). In any event, the exhaust valves 52 may be operated to produce a sealed environment in one, some, or all of the corresponding cylinder during combustion and to allow exhaust gas to exit the cylinder during and/or after combustion (e.g., the controller 5 may operate the exhaust valves 52).

The engine according to one or more embodiments may include one or more sensors (e.g., oxygen sensors) to detect presence and/or amount of oxygen in the exhaust gas. For instance, the engine 10 includes an exhaust or oxygen sensor 54 attached to the exhaust lines 50, such that the sensor 54 may detect and/or measure the amount of oxygen in the exhaust gas passing through the exhaust lines 50 into the exhaust manifold 20. It should be appreciated that, generally, the engine may include any number of suitable sensors, which may detect and/or measure composition of the exhaust gas (e.g., as the exhaust gas passes from the cylinder into the exhaust manifold), temperature of the exhaust gas, etc. In an example, the engine 10 may include one or more so-called "five gas sensors," which may detect and/or measure the composition of the exhaust gas (e.g., sensors configured to detect or identify carbon dioxide (CO2), carbon monoxide (CO), oxides of nitrogen (NOx), etc.).

In the illustrated embodiment, fuel lines 24 connect to a distribution rail 22. For example, the distribution rail 22 is operably or fluidly connected to a fuel supply reservoir (e.g., fuel tank). As such, fuel may be distributed (e.g., pumped) from the fuel supply reservoir to the distribution rail 22 and subsequently into the fuel lines 24. As described above, from the fuel lines 24, the fuel may be injected directly into the cylinders of the engine 10 (e.g., the fuel in the fuel lines 24 may be pressurized and a fuel injector 30 may control injection of the fuel into the cylinders).

As described above, in the illustrated embodiment, the engine 10 includes air lines 26, which may be sized and configured to inject a suitable amount of air into the cylinders of the engine 10. Moreover, air lines may be connected to the intake manifold (e.g., air lines 26 of the engine 10 are connected to the intake manifold 16). In an embodiment, the intake manifold 16 may be positioned opposite to the exhaust manifold 20. It should be appreciated that the intake manifold and the exhaust manifold may be positioned at any location and/or orientation relative to the engine as well as relative to each other.

Generally, the engine according to one or more embodiments may include one or more sensors for identifying or sensing incorrect combustion and/or detonation of the fuel in one, some, or all of the cylinders. In the illustrated embodiment, as shown in FIGS. 2 and 3, the engine 10 includes knock sensors 56 associated with the cylinders thereof to detect detonation of the fuel in the corresponding cylinders. For example, the controller 5 may adjust amount of injected fuel, timing of fuel injection, amount of injected air, timing of air injection, timing of spark in the cylinder, or combinations thereof at least in part based on a signal received from the knock sensors 56. Moreover, it should be appreciated that one, some, or all of the sensors described herein may be coupled to and/or operated by the controller 5. Moreover, as described below in more detail, the controller 5 may control fuel pressure, fuel injectors, air pressure, exhaust pressure, air injectors, spark plugs, etc., at least in part based on the signal or information received from the sensors.

Figure 4:
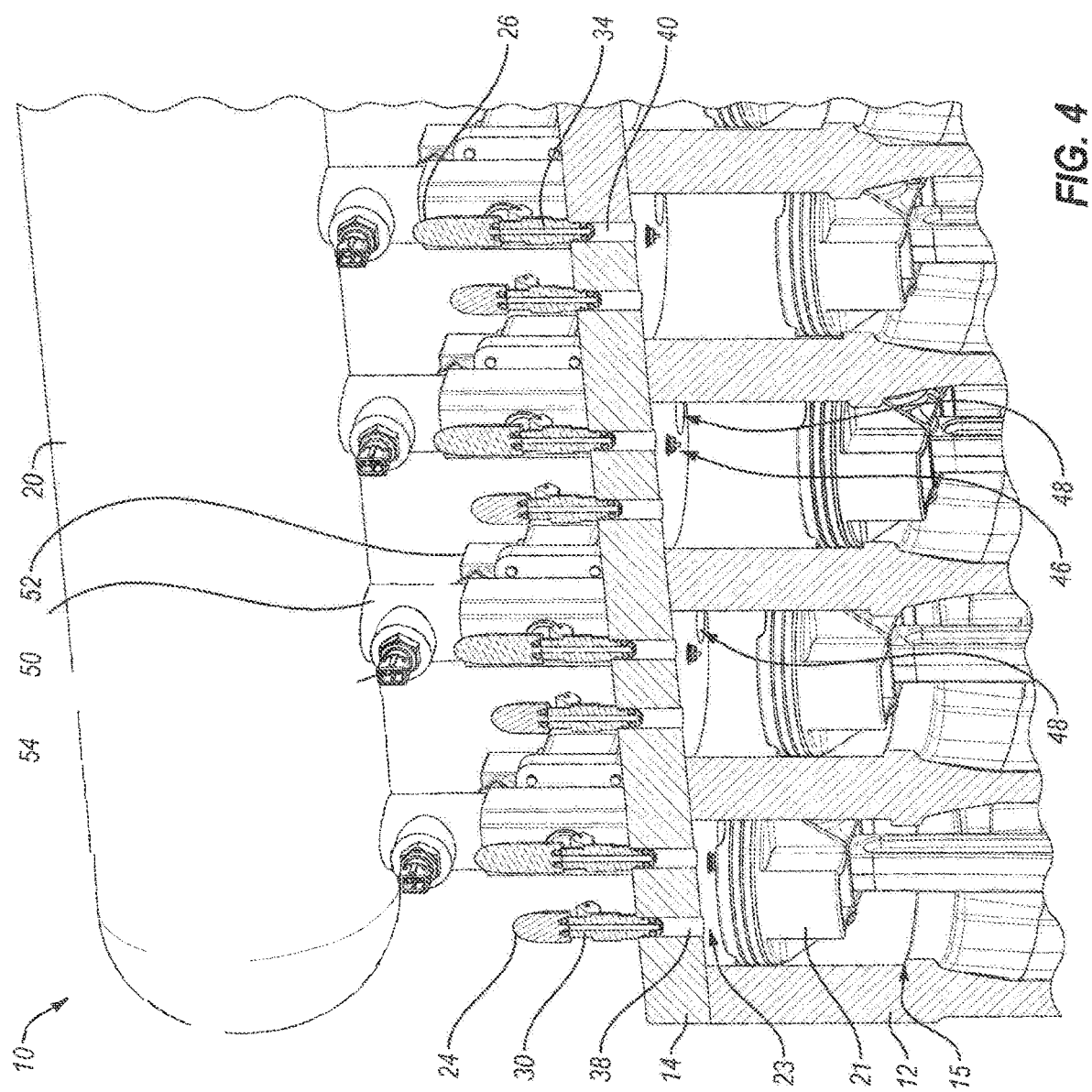
FIG. 4 is a partial longitudinal cross-sectional view of the internal combustion engine of FIG. 1.
Figure 5:
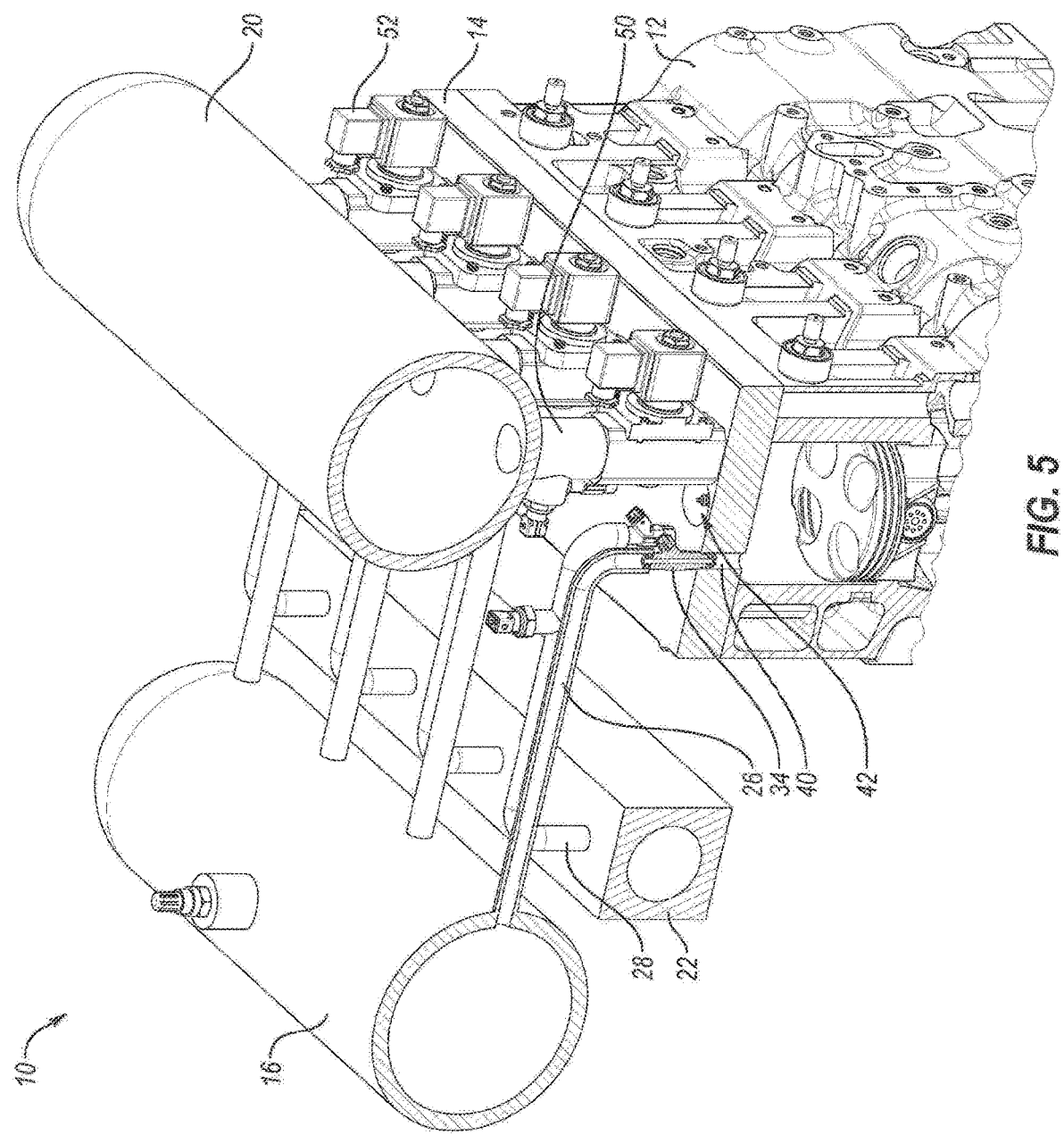
FIG. 5 is a partial transverse cross-sectional view of the internal combustion engine of FIG. 1.

FIG. 4 is a partial longitudinal cross-sectional view of the engine 10 (i.e., cross-section passing through multiple cylinders along the length of the engine 10), and FIG. 5 is a transverse cross-sectional view of the engine 10 (i.e., passing through a single cylinder and along the width of the engine 10) according to an embodiment. As shown in FIGS. 4-5 and described above, the engine 10 includes cylinders 15 and corresponding pistons 21 that may reciprocate in the cylinders 15, thereby rotating the crankshaft and generating mechanical power output of the engine 10.

As mentioned above, the combustion chambers of a reciprocating engine may be formed by the cylinders and corresponding pistons. For example, the engine 10 includes combustion chambers 23 formed or defined by the cylinders 15 and corresponding pistons 21. It should be appreciated that the actual volume of the combustion chamber may change depending on the position of the piston therein during ignition and/or combustion of fuel (e.g., as the piston reciprocated between bottom dead center and top dead center positions in the cylinder). Moreover, as discussed below in more detail, combustion volume within the combustion chamber may depend on the amount of air injected in the cylinder. In other words, the combustion volume may be the volume of the gas (e.g., air) in the combustion chamber when the gas is at atmospheric pressure.

Generally, fuel may be directly injected into the cylinders 15. For example, the fuel may be injected directly into the cylinders through corresponding fuel ports, which may open into the corresponding cylinders of the engine. In the illustrated embodiment, the engine 10 includes fuel ports 36 that open directly into the cylinders (e.g., from the cylinder head 14). More specifically, the fuel lines 24 connect to corresponding fuel injectors 30 located and/or secured in the fuel injection ports 38. In an embodiment, the fuel injectors 30 may be operated to allow or restrict fuel flow or injection from the fuel lines 24 into the corresponding cylinders 15. It should be also appreciated that, the engine may include any number of suitable mechanisms for injecting fuel into the cylinders.

In addition to or in lieu of directly injecting fuel into the cylinder, in some instance, air may be injected directly into the cylinders of the engine. In the illustrated embodiment, the engine 10 includes air injection ports 40 that open into the corresponding cylinders 15 (e.g., from the cylinder head 14). For example, the air lines 26 are connected to one or more corresponding air injectors 34, which may inject air directly into the corresponding cylinders 15 through the air injection ports 40. In some instances, the air injectors 34 are positioned and/or secured in the corresponding air injection ports 40 and may be configured to inject air thereto from air lines 26. As mentioned above, the controller may control operation of the air injectors 34 (e.g., timing of the injection, duration and/or amount of the injection, etc.).

Generally, air and/or fuel may injected into the cylinder at any number of suitable angles and/or locations. For example, at least some of the air may be injected such as to form a swirl effect that may facilitate mixing the air with the fuel inside the cylinder. In an embodiment, the air and/or fuel may be injected from a location or ports in the cylinder head (e.g., air may be injected along a generally parallel direction relative to the movement of the piston 21, which may include one or more pockets or recesses that may direct the air in a manner that produces a swirl effect inside the cylinder). Alternatively or additionally, at least some of the air and/or fuel may be injected along a generally perpendicular direction relative to the movement of the piston 21. For example, air may be injected at a location substantially opposing the location of the fuel injection. Furthermore, it should be appreciated that the air injectors 34 and/or the fuel injectors 30 may correspondingly inject air and fuel at multiple angles and/or at a spray angle or fan, such as to facilitate mixing of the air and fuel inside the cylinder.

The air injectors 34 may include any suitable valve and/or gaging mechanism that may regulate and/or control air injection into the corresponding cylinders. In some embodiments, the air injectors 34 may be similar to or the same as fuel injectors (e.g., GDI injectors). For example, the fuel injectors may be similar to or the same as commercially available GDI or FSI fuel injectors, such as FSI fuel injectors (e.g., manufactured by Bosch), Diesel Direct Injectors, etc., which may be electrically or electronically controlled (e.g., by the controller 5) and may be operably connected to the fuel supply (e.g., via a distribution elements, such as the distribution rail 22).

In any event, the air injectors 34 may be configured to be controlled to allow a predetermined and/or controlled amount of air from the air lines 26 into the corresponding cylinders 15 of the engine 10. Moreover, injection of air into the cylinders may be generally unobstructed. For example, as noted above, the injection ports 40 open directly into the cylinders, without any obstruction that may interfere with or impede air flow into the cylinders 15. Alternatively, in some embodiments, the engine may include one or more obstructions or redirection mechanisms (e.g., baffles) that may guide and/or distribute the air in the cylinders 15

In some embodiments, the controller may regulate or control the amount of air (e.g., a volume of air at a selected pressure or mass of air) injected into the corresponding cylinders 15 and produce a predetermine combustion volume. Hence, under some operating conditions, the controller may operate the air injector 34 to inject an amount of air that may have the same volume as the volume of the cylinder (e.g., the volume of the cylinder when the piston 21 is at bottom dead center). In some instances, the controller 5 may operate the air injectors 34 to inject the amount of air that may have a greater volume (e.g., at atmospheric pressure) than the volume of the cylinder 15 (e.g., thereby increasing the operating volume of the cylinder 15).

Moreover, in some examples, the controller 5 may operate the air injectors 34 to inject the amount of air that may be less than the volume of the cylinder 15 (e.g., thereby decreasing the operating volume of the cylinder 15 and/or producing below atmospheric pressure in the cylinder 15). It should be also appreciated that reducing the pressure in the cylinder 15 to below atmospheric (e.g., operating the cylinder 15 at partial vacuum at some portions of the operating cycle) may improve or aid in vaporizing the fuel that may be injected into the cylinder 15, thereby improving combustion.

In some embodiments, as shown in FIGS. 4-5, the fuel and/or air injection ports 38, 40 and/or corresponding fuel and air injectors 30, 34 are oriented approximately parallel to the movement of the pistons 21. Additionally or alternatively, the fuel and/or air injection ports and/or corresponding fuel and air injectors may have non-parallel orientation relative to the movement of the pistons 21. Furthermore, in some examples, the fuel and/or air injection ports and/or corresponding fuel and air injectors may be located in one or more sidewalls of the cylinder.

In one or more embodiments, one, some, or each of the cylinders of the engine may have multiple fuel and/or air injection ports. In any event, the fuel and/or air injection ports may have any suitable orientation relative to a center axis of the cylinder or to movement of the piston in the cylinder. As such, fuel and/or air may be injected into the cylinder in a manner that may produce a suitable distribution thereof in the cylinder (e.g., optimize distribution). In some examples, the fuel and/or air injectors may be operated sequentially or asynchronously to produce a suitable distribution and/or mixing of the fuel and air in the cylinder.

As mentioned above, the air and/or fuel may be injected into the cylinders, generally, unobstructed (e.g., through corresponding fuel and air injection ports 38, 40, which may be substantially unobstructed by valves or other elements or components of the engine 10). Hence, the amount of air and/or fuel injected into the cylinder may be precisely or better controlled (e.g., as compared with conventional engines including valves). Additionally or alternatively, injection velocities of the fuel and/or air may be controlled to produce suitable mixing thereof in the cylinder. For instance, fuel and/or air may be injected into the cylinder(s) in any number of suitable sequences or stages of injection(s) and/or at any number of suitable angles (relative to the cylinder and/or to one another).

Moreover, while, in some embodiments, the fuel and air may be injected into the cylinders through separate or individual injection port and may mix in the cylinder, this disclosure is not so limited. For example, the air and fuel may enter one, some, or all of the cylinders from the same port (e.g., each cylinder may include a single port for injecting both air and fuel therethrough). In an embodiment, the air and fuel may be at least partially premixed before entering the cylinder (e.g., the air and fuel may be at least partially premixed near the injection port).

In an embodiment, the engine 10 includes one or more spark plugs 46 to ignite the fuel-air mixture in the corresponding cylinders 15. For example, threaded openings may open into the cylinder 15 (e.g., from the cylinder head 14) and may secure corresponding spark plugs 46 relative to the cylinder 15. In any event, in some instances, the spark plugs 46 may be operated to ignite the fuel-air mixture in the corresponding cylinders 15 (e.g., a controller may control and/or supply power to the spark plugs based on a selected, predetermined, and/or adjustable timing).

In one or more embodiments, one, some, or all of the cylinders 15 of the engine 10 may operate without the spark plug 46 and/or without operating one, some, or all of the spark plugs 46. For example, diesel may be injected into one, some, or all of the cylinders 15 of the engine and may be ignited and combusted without spark ignition. Moreover, in an embodiment, one or some of the cylinders 15 may receive gasoline, which may be ignited by a spark from the corresponding spark plugs 46, while one or some of the cylinders 15 may receive diesel, which may be combusted during compression thereof (e.g., without operating the corresponding spark plugs 46).

In some examples, the spark plugs 46 may be at least partially recessed in the cylinder head 14. For instance, the cylinder head 14 may include recesses 42, which may be connected to or extend from corresponding threaded openings. As mentioned above, the spark plugs 46 may be screwed into the threaded openings, such that spark generating portions of the spark plugs extend into the corresponding cylinders 15.

As described above, exhaust gas from the cylinders 15 may exit into the exhaust manifold 20. In the illustrated embodiment, the engine 10 includes exhaust ports 48 in fluid communication with one, some, or each cylinder 15. In some examples, the exhaust ports 48 are in fluid communication with the corresponding exhaust lines 50, which may be connected to the manifold 20. Hence, the exhaust gas produced during combustion of fuel may exit the cylinders 15 through the exhaust ports 48, into the exhaust lines 50, and further into the exhaust manifold 20. In any event, the exhaust gas may exit the cylinders 15 through corresponding exhaust ports 48.

In some instances, the engine 10 may include exhaust valves 52, which may selectively open and/or close flow at and/or through the exhaust ports 48 (e.g., one, some, or all of the exhaust valves 52 may be electrically or electronically controlled by the controller). More specifically, in some embodiments, closing the exhaust valves 52 provides at least partially sealed or hermetic environment in the corresponding cylinders 15 (e.g., during combustion of the fuel). Conversely, for example, opening the exhaust valves 52 allows the exhaust gas in the corresponding cylinders 15 to exit and/or to be withdrawn therefrom.

Figure 6:
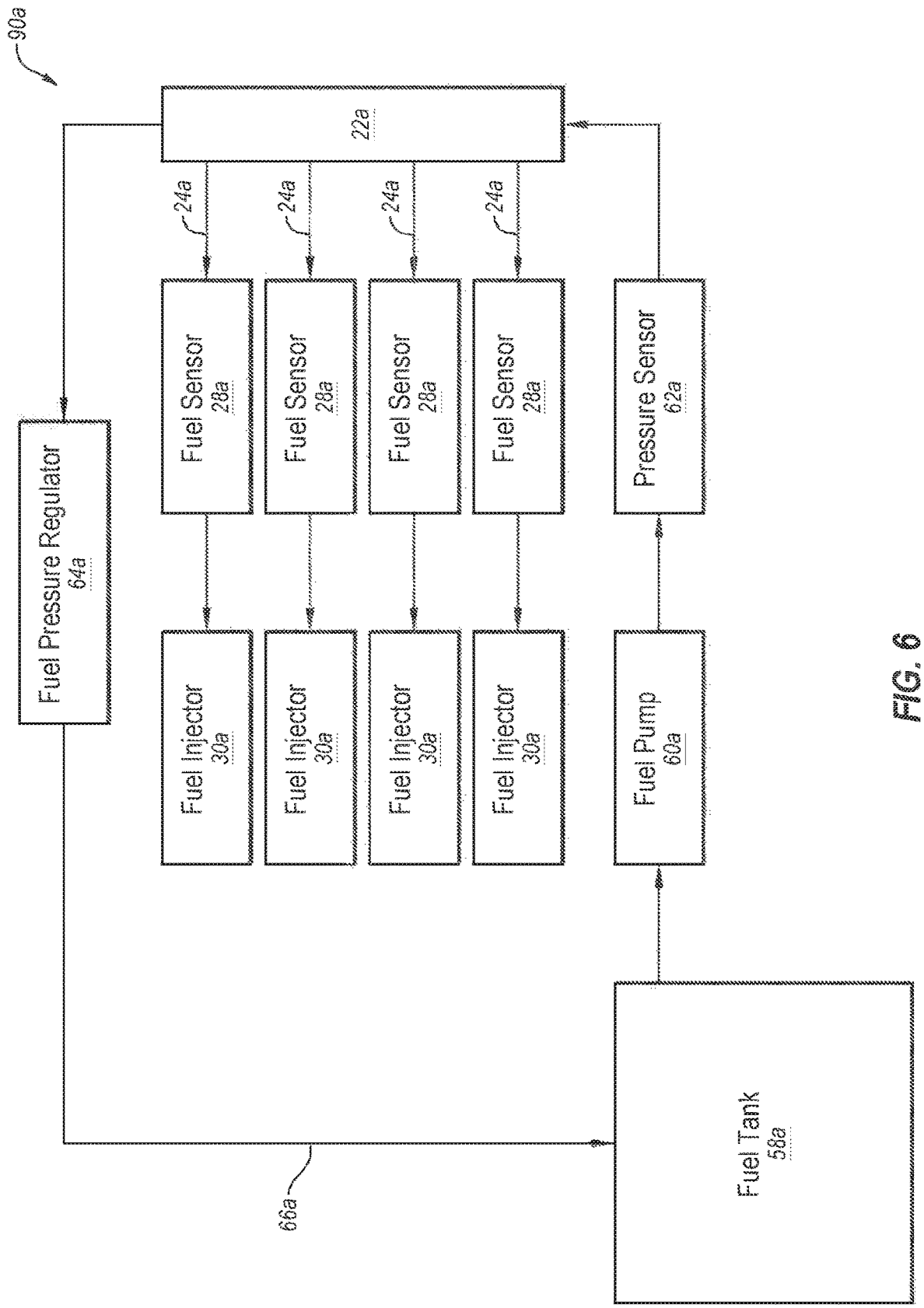
FIG. 6 is a schematic block diagram of a fuel system according to an embodiment.

The operation of the engine and/or components or elements thereof also may be represented schematically. For example, the engine may include or may be connected to a fuel system 90a, which is represented schematically with a block diagram shown in FIG. 6. As mentioned above, the engine may include any number of cylinders, which may vary from one embodiment to the next. For easy of description, the block diagram of FIG. 6 illustrates the fuel system 90a that is included or connected to a four cylinder engine.

In an embodiment, fuel in the fuel system 90a is pumped from a fuel tank 58a by a pump 60a. It should be appreciated that, in some embodiments, the fuel may be advanced from the fuel tank with any number of suitable devices or configurations (e.g., the fuel may be gravity fed from the fuel tank). Additionally or alternatively, in the illustrated embodiment, the fuel system 90a includes a pressure sensor 62a (e.g., in fluid communication with the fuel) to measure the pressure of the fuel in the fuel lines (e.g., directly after the fuel exits the fuel pump 60a).

In an embodiment, the fuel pump 60a is in fluid communication with and may pump the fuel into the distribution rail 22a. As described above, the distribution rail 22a is connected to the fuel into fuel lines 24a and may distribute fuel thereto. The fuel lines 24a may distribute the fuel toward and/or into corresponding cylinders engine. In an embodiment, the fuel system 90a includes a fuel pressure regulator

64a, which may regulate the pressure in the fuel lines 24a and/or in the distribution rail 22a. For example, the fuel pressure regulator 64a may facilitate maintaining an approximately constant pressure in the fuel rail 22a and/or in the fuel lines 24a.

In some instances, the fuel pressure regulator 64a may release or reduce fuel pressure in the lines and/or distribution rail 22a to produce a suitable and/or selected and/or predetermined pressure therein. For example, the fuel pressure regulator 64a may reduce pressure in the distribution rail 22a by allowing some fuel to exit the distribution rail 22a. In some embodiments, the fuel exiting the distribution rail 22a may flow or may be pumped back to the fuel tank 58a (e.g., along a return line 66a).

In at least one embodiment, the fuel system 90a includes one or more fuel sensors 28a that correspond to the fuel lines 24a leading to the cylinders of the engine. For instance, the fuel sensors 28a may detect the fuel type in the fuel lines 24a. Also, as described above, the fuel may be injected into the cylinders by or through fuel injectors 30a. For example, the controller may determine the duration of time the fuel injectors 30a remain open, such that a selected and/or predetermined amount of fuel enters the respective cylinders of the engine. It should be appreciated that the controller also may actuate any of the fuel injectors 30a at any time and for any duration of time (e.g., to produce customized injection of fuel for each cylinder). Moreover, the controller may operate the fuel injectors 30a at least in part based on the signal or reading from one, some, or all of the fuel sensors 28a.

Figure 7:
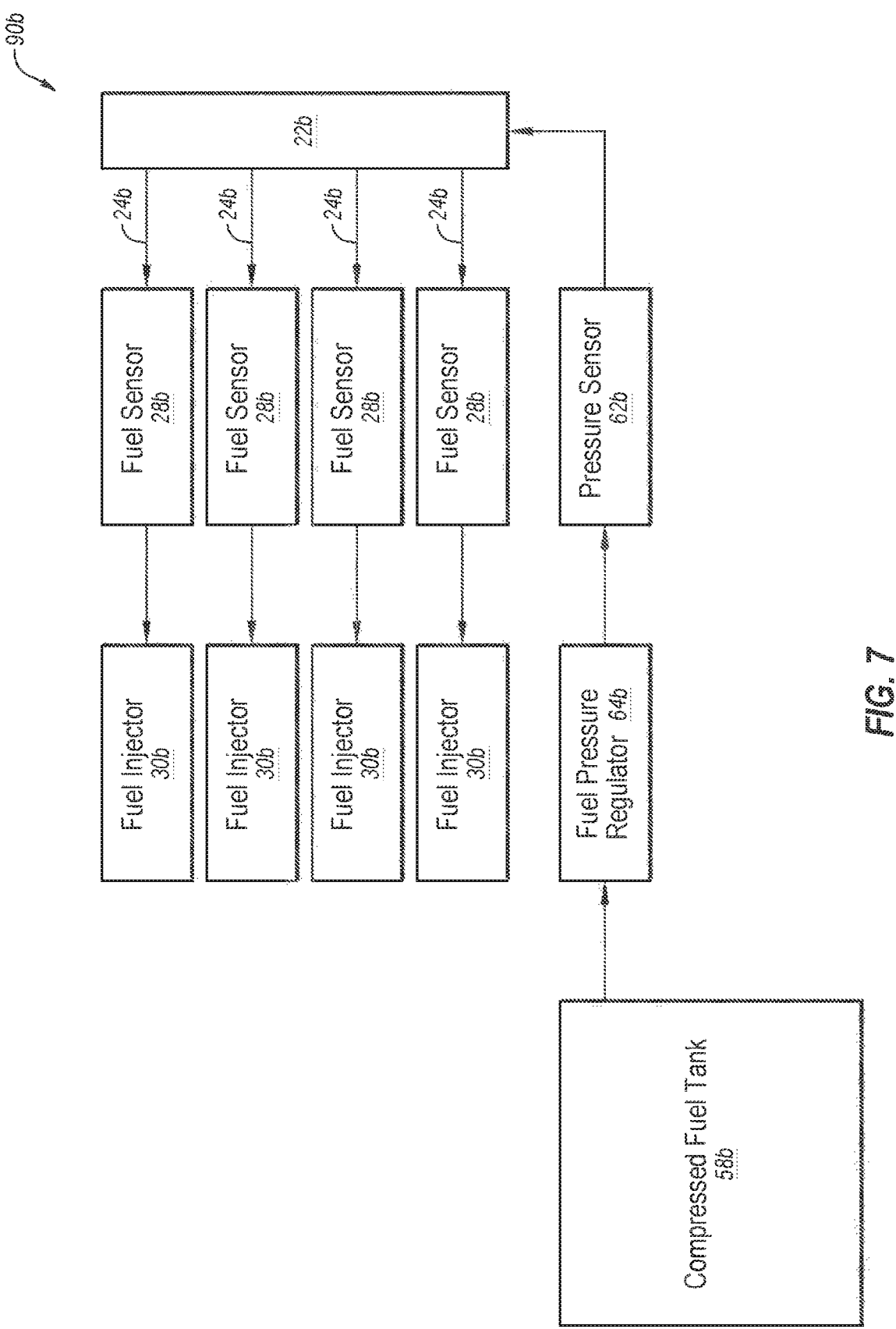
FIG. 7 is a schematic block diagram of a fuel system according to another embodiment.

While in some embodiments the fuel pressure regulator may be located sequentially after the distribution rail 22 (e.g., downstream of the fuel flow), this disclosure is not so limited. FIG. 7 a schematic block diagram of a fuel system 90b according to one or more embodiments. As shown in FIG. 7, in at least one example, a fuel pressure regulator 64b is located between the distribution rail 22b and a compressed gas tank 58b (e.g., compressed gaseous fuel may be located in the compressed gas tank 58b). In an embodiment, the fuel in the compressed gas tank 58b may be pressurized by a fuel pump (if in liquid phase) or by a compressor (if in gas phase) and may be maintained at an approximately constant and/or selected and/or predetermined pressure in the compressed gas tank 58b. Furthermore, in some embodiments, the fuel system 90b may include one or more mechanisms for maintaining the fuel (e.g., in the distribution rail, in the fuel lines, etc.) at an approximately constant pressure.

The fuel pressure regulator 64b may be operated by the controller to produce or generate fuel flow from the compressed gas tank 58b into the distribution rail 22b (e.g., as regulated by the controller at least in part based on the signals or information from the pressure sensor 62b). For instance, the fuel pressure regulator 64b may be operated in a manner that the fuel in the distribution rail 22b and/or in the fuel lines 24b is at an approximately constant pressure.

Figure 8:
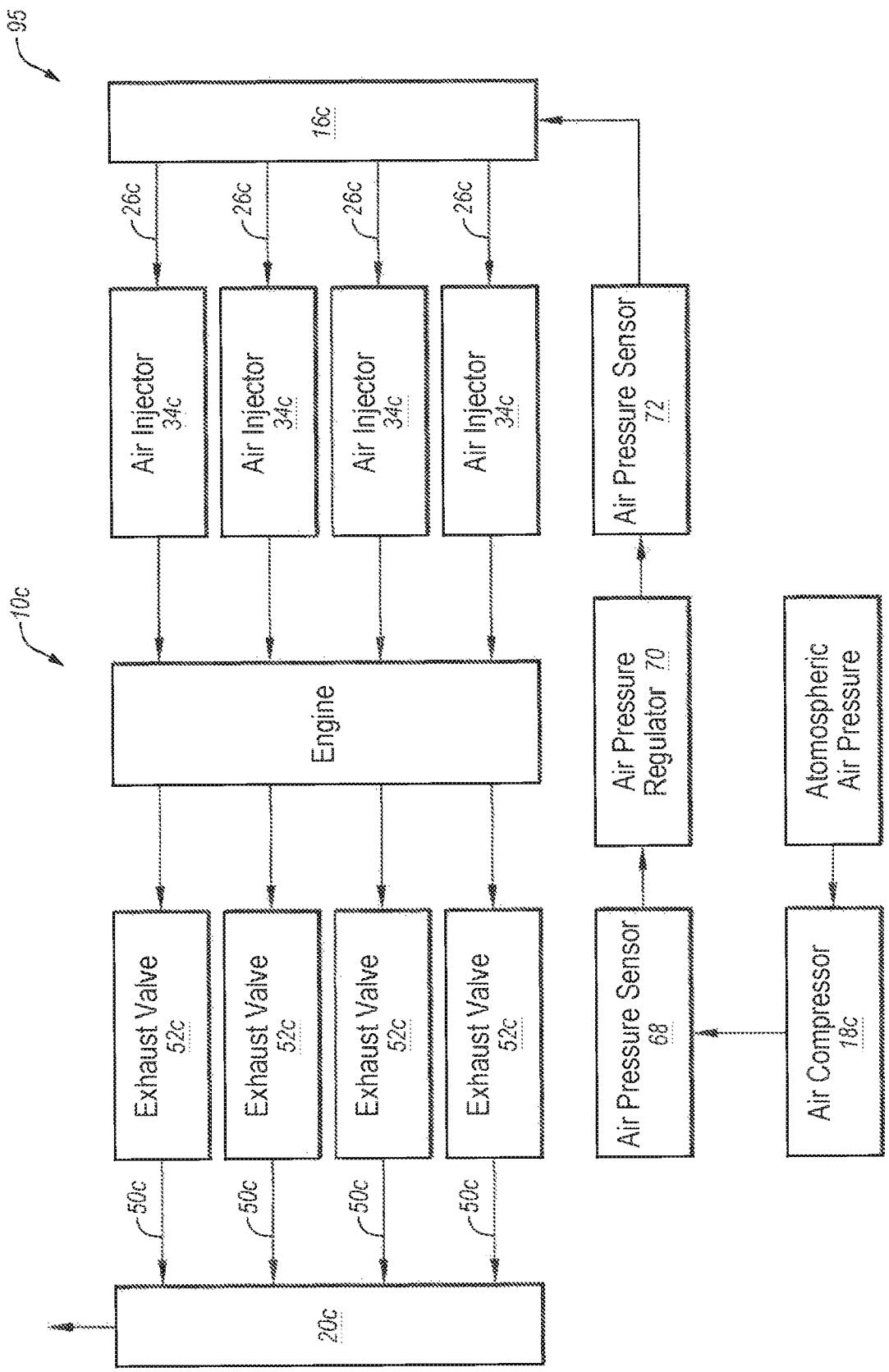
FIG. 8 is a schematic block diagram of an air system according to an embodiment.

As described above, the engine may include or may be connected to an air injection system. FIG. 8 illustrates a schematic block diagram of an air injection system 95 according to an embodiment. In the illustrated embodiment, the air injection system 95 includes compressor 18c, which may draw air (e.g., at atmospheric pressure) and output pressurized air (e.g., at a pressure that is greater than the atmospheric pressure). In some embodiments, the air injection system 95 includes a first air pressure sensor 68 that may detect output air pressure of the air compressor 18c.

Hence, the controller may regulate operation of the compressor 18c based at least in part on the readings or signals from the air pressure sensor.

In some examples, the air injection system 95 includes an air pressure regulator 70 that may regulate the pressure between the air compressor 18c and the intake manifold 16c. For example, the air pressure regulator 70 may be set to a selected and/or predetermined pressure or may be dynamically and/or automatically adjusted (e.g., by the controller) during operation of engine 10c. In at least one embodiment, the air injection system 95 includes a second air pressure sensor 72, which may verify the air pressure in the intake manifold 16c. For instance, the controller may adjust the air pressure regulator 70 at least in part based on the readings or information from the second air pressure sensor 72, such as to produce a selected, predetermined, and/or suitable pressure in the intake manifold 16c and in air lines 26c that supply air to the corresponding cylinders of the engine 10. In an embodiment, the air in the intake manifold 16c and/or in the air lines 26c may be maintained at an approximately constant pressure.

In one or more embodiments, air injection into the cylinders of the engine may be controlled and/or regulated by air injectors 34c. As described above, the air injectors 34c may control the amount of air that is injected from the air lines 26c into corresponding cylinders at any one or more times during the engine's cycle. For example, the controller may actuate one, some, or all of the air injectors 34c at any suitable time and for any suitable duration of time to allow a suitable or selected and/or predetermined amount of air from the air lines 26c to flow through the corresponding air injectors 34c and inject into the cylinders of the engine 10c.

In some embodiments, the engine may idle for a period of time using compressed air to power it. In other words, the compressed air may be injected into the cylinders by sequentially operating the air injectors 34c in a manner that forces pistons downward in a sequence that produces rotation of the crankshaft. In an example, the compressed air may be used to start or assist in starting the engine (e.g., in the event a starter is disabled or battery power is not available to the starter). For instance, compressed air may be supplied from a tank (e.g., a reserve tank) that may contain pressurized air. Moreover, in some examples, during operation of the engine, air may be continuously added to and/or circulated from the tank (e.g., from the operation of the engine, which may produce compressed air and/or from the air compressor).

As mentioned above, the engine 10c may include or may be connected to an exhaust system. For example, the exhaust from the cylinders may enter the corresponding exhaust line 50c and may flow into the exhaust manifold 20c. In some embodiments, the exhaust manifold 20c may be connected to one or more additional components or elements of the exhaust system (e.g., catalytic converter, muffler, etc.).

In an embodiment, one, some, or all of the air injectors, fuel injectors, exhaust valves, or combinations thereof may be mechanically decoupled or disconnected from an output shaft (e.g., from the crankshaft) and/or may be operated (including directly or indirectly, such as by providing instructions for operating) by a controller. Generally, the controller may be any suitable general purpose or special purpose computing device, which may be programmable. For example, the controller may include one or more processors, memory (e.g., storage memory, RAM, etc.) operably coupled to the processor(s), and an input/output (I/O) interface for receiving and sending commands or signals. In any event, the controller may be configured to operation of one or more elements or components of the engine (e.g., at least in part based on the information or signals from the sensors described herein).

In an embodiment, the controller may regulate the operation of fuel injectors, air injectors, exhaust valves, or combinations thereof based on any number of suitable parameters and/or inputs. In an embodiment, the engine or combustion system may include and/or may be connected to a throttle position sensor, which may detect a change in position of a throttle indicator (e.g., a gas pedal). Moreover, a crankshaft position sensor may detect position of the crankshaft and may provide information about crankshaft position to the controller (e.g., based on the crankshaft position, the controller may determine the respective positions of the pistons in one, some, or all of the cylinders of the engine). In any case, based on any number of suitable parameters and/or inputs, the controller may adjust operation of the engine or any portion thereof (e.g., supply of fuel and/or air to one or some of the cylinders may be different from one or some of the other cylinders and/or any one or some of the cylinders may be disabled at any time).

It should be appreciated that, according to one or more embodiments, actuation of the fuel and air injectors and the time for which they remain actuated or open may be controlled in a manner that provides fuel and/or air in stages to each cylinder. For instance, a first charge of fuel and/or air may be provided at a first position of the piston, after the piston has completed its upward stroke (e.g., top dead center) and as the piston moves down during the down stroke; as the piston moves further down, during the down stroke, one or more additional charges of fuel and/or air may be provided into the cylinder at one or more additional positions of the piston, before the piston reaches the end of downward stroke (e.g., bottom dead center). Furthermore, additional or alternative charges of fuel and/or air may be supplied into the cylinder prior to the piston reaching the top or bottom dead center (e.g., various configuration and staging settings may configure the engine to be adjustable to the burning characteristics of different fuels).

In some examples, the engine may be operated to produce a rapid increase in power of short duration (e.g., by operating the engine on a two-stroke cycle). For example, the fuel and air may be injected each time a piston commences a downward stroke (instead of every alternate stroke of the four-stroke cycle). Moreover, any one or more cylinders may be operated on two-stroke cycle to generate a rapid increase in power output from the engine.

As described above, generally, the internal combustion engine includes at least one combustion chamber and an output shaft rotatable in response to combustion of fuel in the combustion chamber(s). For example, the internal combustion engine may include an energy conversion mechanism for converting the energy produced during combustion of a fuel in the combustion chamber(s) into mechanical output at the output shaft (e.g., converting pressure increase in the combustion chamber into rotation of the output shaft). In an embodiment, the fuel and oxidizer are injected into the combustion chamber and a combustion reaction produces a pressure increase therein; the energy conversion mechanisms configured to convert the increased pressure in the combustion chamber into mechanical energy, such as rotation of the output shaft (e.g., pistons movable in cylinders and connected to the output shaft; a housing and rotatable rotor connected to the output shaft, etc.).

In any event, in one or more embodiments, a controller or control system may control operation of the internal combustion engine by controlling injection of the fuel and/or air into the combustion chamber and/or by controlling exhaust from the combustion chamber. For example, the controller may control the engine that may include one or more fuel injectors and/or one or more air injectors, which may respectively inject fuel and oxidant into the combustion chambers (e.g., cylinders) of the engine and exhaust valves that may prevent or allow exhaust to exit corresponding combustion chambers. As described below in more detail, in at least one embodiment, the fuel injectors, air injectors, exhaust valves, or combinations thereof are mechanically decoupled or disconnected from the output shaft and may be operated by the controller. Also, generally, controlling the amount of injected fuel and/or air into the cylinders as well as timing of such injections may produce any number of suitable operating conditions for the engine.

In some embodiments, the controller may be operably coupled to one or more elements or components of the engine and/or may control or actuate operation thereof. For instance, a control system that includes the controller may include any number of suitable sensors that may provide various inputs to the controller. In some examples, the control system includes one or more input interface devices (e.g., a device including a user interface) coupled to the controller, such that the controller may receive input therefrom (e.g., input that may be provided by a user and/or may be related to an operating parameter of the engine). Hence, the controller may receive one or more inputs and may operate (directly or indirectly) elements or components of the engine (and/or elements or components connected to the engine) and, thereby, modify operation of the engine. For example, the controller may modify or adjust operation of the engine to change and/or optimize power output, number of revolutions per minute (RPM) of the output shaft, direction of rotation of the output shaft, combustion efficiency, combustion volume, combination of the foregoing, etc.

In one or more embodiments, the control system may determine or calculate an amount of fuel and/or air to be injected into the cylinders of the engine based on one or more operation inputs (e.g., inputs from the user of the engine). For example, operation inputs may include inputs related to a power output requirement, RPM of the output shaft, combustion volume, etc., and the control system may determine parameters for the engine's elements and/or components to achieve or produce the operation of the engine that corresponds with the operation input(s). For instance, as described below in more detail, the controller may determine the amount of fuel and/or air to inject into the cylinders and/or timing of such injection(s), timing of ignition of the air-fuel mixture in the cylinders, timing and duration of openings of exhaust valves, etc.

Generally, the internal combustion engine may combust any suitable type of fuel, such as gasoline (petrol), ethanol, diesel, liquefied natural gas (LNG), liquefied petroleum gas (LPG), hydrogen, etc. Moreover, any suitable oxidizer, such as oxygen, may facilitate and/or promote combustion of the fuel.

As discussed above, the combustion engine 10 (e.g., as shown in FIG. 1) may be computer controlled and may be operably coupled to the controller 5, according to an embodiment. Again, it should be appreciated that the engine may have any number of cylinders and any number of suitable cylinder arrangements, as discussed above (e.g., V, rotary, boxer, etc.).

As described above, the fuel and/or air may be injected directly into the cylinders of the engine 10. For example, the engine 10 includes fuel injectors 30 and air injectors 26 (FIG. 4) that are associated with corresponding cylinders of the engine 10. In some embodiments, the controller 5 operates (which includes operating directly or indirectly, such as by providing instructions for operating) the fuel injector 30 and/or air injectors 26, as described below in more detail.

As described above, the air injectors 26 may be connected to any number of sources or supplies of air or any number of suitable oxidants. In one or more embodiments, the air injectors 26 connect to an air intake manifold 16. For example, the air intake manifold 16 may contain and/or distribute air (e.g., compressed air) to the air injectors 26 (e.g., via one or more corresponding air lines between the air injectors 26 and the intake manifold 16. In some embodiments, the air intake manifold 16 may be in fluid communication with a compressor 18, which may supply compressed air into the air intake manifold. Analogously the fuel injectors 30 may be connected to a supply of fuel (e.g., a fuel pump may supply fuel to or toward the fuel injectors 30).

In one or more embodiments, the controller 5 operates (directly or indirectly, such as by providing instructions for operating) the fuel injector 30 and/or air injectors 26, as described below in more detail. For example, the exhaust valves 52 of the combustion engine 10 may be operably coupled to the controller 5 and may be operated thereby between open and closed positions, such that in the open positions exhaust may exit the cylinder during and/or after combustion, and in the closed position the exhaust valves 52 at least partially prevent exhaust from exiting the corresponding cylinders. Furthermore, as mentioned above, the controller 5 may be connected to one or more sensors that may provide information about operation of the engine 10 and/or about operating parameters for the operation of the engine 10. In some embodiments, an octane or fuel sensor is connected to the controller 5 and positioned in contact with the fuel flowing toward or to the fuel injector 30 (FIG. 4). Hence, the controller 5 may receive information or signals related to the fuel flowing toward and/or to the cylinders of the engine 10.

The controller 5 may also be connected to one or more sensors that may provide information about the oxidant being supplied to the cylinders of the engine 10. For example, the engine 10 may include a pressure and/or temperature sensor 17 connected to the controller 5 and in communication with the air in the intake manifold 16. Similarly, the controller 5 may be connected to one or more sensors that may provide information about the exhaust exiting one or more cylinders of the engine 10.

In an embodiment, the engine 10 includes exhaust sensors 54 in communication with the exhaust exiting corresponding cylinders of the engine 10 and connected to the controller 5. For example, the exhaust sensors 54 may detect or determine the amount of oxygen present in the exhaust gases exiting the corresponding cylinders of the engine 10. Furthermore, in some examples, the controller 5 may be connected to one or more oxygen sensors in communication with the incoming air (e.g., air in the intake manifold 16, in air lines connecting the intake manifold 16 to the air injectors 26). Hence, the controller may receive input or signals related to the oxygen content or concentration in the air flowing toward or to injection in the combustion chambers of the engine 10.

As described below in more detail, the controller may be connected to and/or receive information from any number of suitable sensors, such as position sensors connected to the output shaft, knock sensors, throttle position sensors, etc. Moreover, in some examples, the controller may receive input from sensors and/or input devices that may be unassociated with the engine. In any event, the controller may operate the air injectors, fuel injectors, exhaust valves, or combinations thereof at least in part based on the information or signals received from the sensors connected to the controller.

Figure 9:
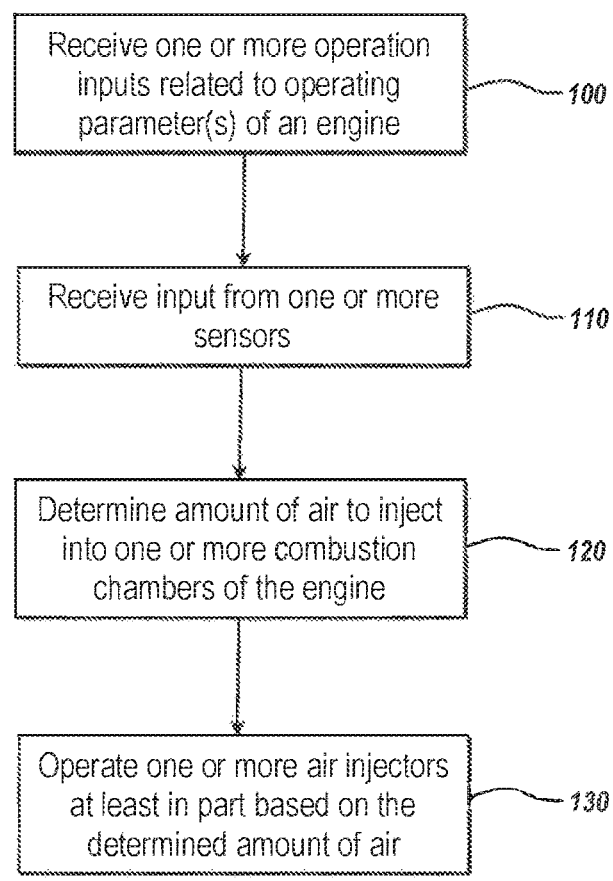
FIG. 9 is a flow chart of a method of controlling operation of an internal combustion engine according to an embodiment.

FIG. 9 illustrates a flow chart of operations or acts that may be performed by a controller of a control system, which may control combustion in and/or operation of the internal combustion engine, according to at least one embodiment. In an embodiment, the controller performs or executes an act 100 of receiving one or more operation inputs related to an operating parameter of an engine. For example, the controller may receive input or information related to power output and/or RPM to be produced by the engine (e.g., a request to increase RPM of the engine's crankshaft). Generally, the input may be provided or supplied to the controller in any number of suitable ways and/or from any number of suitable input interfaces and/or input interface devices. For example, in a vehicle, the input interface device may be a throttle (e.g., a throttle pedal, lever, handle, etc.).

In some instances, one or more sensors (e.g., position sensors) may receive input from the throttle and transmit a translated input (e.g., displacement of the throttle) to the control system. Hence, for example, displacement of the throttle pedal (e.g., input from a user) may be digitized or translated into a corresponding input transmitted or sent to the controller that may indicate to the controller the amount of displacement of the throttle pedal produced by the user. In some instances, displacement of the throttle pedal (as indicated by the signal or input from the sensor coupled to the throttle pedal) may be processed and/or associated by the controller with one or more operating parameters of the engine, such as RPM, power output, etc.

Also, because displacement(s) of the throttle pedal may be digitized, combinations or patterns of displacements (e.g., multiple short displacements, multiple long displacement, combinations thereof, etc.) may be correlated by the controller with a particular operating parameter of the engine. For example, two long displacements may be correlated by the controller with a selected and/or predetermined power output or percentage increase of the power output or RPM of the engine. In any event, the controller may receive one or more inputs related to a desired or requested power output and/or RPM of the engine.

In alternative or additional embodiments, the controller may receive an input for a requested combustion volume. For instance, a suitable input interface may include a dial, keyed interface, touchpad, combination of the foregoing, etc. In any case, the input interface may facilitate entry of the desired or requested combustion volume for the engine, which may be sent or transmitted to the controller. In some embodiments, the input related to operating parameter(s) may include a requested sound (e.g., frequency, tonality, etc.) to be produced by the engine. For example, an interface may provide or display sound options (e.g., sounds of various engines or engine models) and receive selection(s) of such options; the interface may transmit to the controller such selections as input related to the operating parameter of the engine.

Moreover, in one or more embodiments, the input(s) may be indirectly related to one or more operating parameters of the engine. For instance, the engine may be included in an engine-driven vehicle. Hence, for example, the input may be related to a speed of the vehicle, which may depend on orientation of the vehicle (e.g., inclined, declined, etc.), maneuvers of the vehicle, weather conditions, etc. In such example, the input from the input interface device (e.g., cruise control) may be translated or converted to one or more parameters or inputs that may be related to operating parameter(s) of the engine, such as RPM of the crankshaft.

In some embodiments, inputs (e.g., inputs that may be indirectly related to the operating parameters of the engine) may be related to and/or at least partially based on anticipated power requirements for the engine. For instance, operation input(s) for controlling an engine of an engine-powered vehicle may relate to and/or may be at least partially based on the weight of the vehicle and its cargo, anticipated or planned route (e.g., uphill, downhill, turns, etc.), etc. Hence, as described below in more detail, the controller may correlate such input with the operating parameter(s) of the engine.

In some embodiments, the operation input(s) may include identifying a particular type of fuel and/or oxidant that will be supplied into the engine's cylinders. For example, inputs may include selections or entries of fuel type and oxidant combinations, which may be received via any suitable interface that may be coupled to the controller. Additionally or alternatively, the input(s) related to the fuel and/or oxidant types may be received from one or more sensors. In some embodiments, the controller performs or executes an act 110 of receiving input from one or more sensors. For instance, the controller may receive input from fuel and/or oxidant sensors. While from time to time the description refers to a "cylinder" or "cylinders," it should be appreciated that such references are made for simplicity and the engine may include any suitable combustion chamber(s), as described above.

In at least one embodiment, the controller may receive input from one or more air pressure sensors, which may indicate pressure in the air lines and/or in air intake manifold that may collectively supply air (or other oxidant) into the cylinders. In other words, the controller may receive information about the pressure or percent compression of the air that may be forced or injected directly into the cylinders (e.g., without interference of valves). In some instances, the controller also may receive input from additional or alternative sensors in communication with the air lines and/or in communication with air intake manifold; such sensors may identify the type of oxidant in the air lines and/or quantity thereof (e.g., percent of Oxygen present in the air). Furthermore, in some examples, the controller may receive input from one or more exhaust sensors. For example, the exhaust sensors may provide input related to oxygen content in the exhaust gases that exit the cylinders of the engine.

In an embodiment, the controller may receive input from fuel sensors that may identify the type of fuel being supplied to the cylinders. For example, the fuel sensors may be in communication with fuel and may identify the type thereof (e.g., distinguishing gasoline, diesel, hydrogen, natural gas, propane, etc.). In some instances, one or more sensors also may determine or identify pressure of the fuel (e.g., in the fuel lines, near the fuel injectors, etc.).

In some embodiments, the controller may receive input or signals related to the engine temperature, air temperature, fuel temperature, etc. For instance, the controller may receive information related to the temperature of the engine from one or more sensors (e.g., thermocouples) in thermal communication with one or more portions of the engine. In additional or alternative embodiments, the controller may receive input about the rotational speed (RPM) and/or position of the engine's crankshaft. For instance, one or more encoders or similar sensors may be connected to the crankshaft and may determine the rotational position of the crankshaft as well as the rotational speed thereof. Furthermore, an example, the encoders may be absolute encoders and may maintain positional information related to the position of the crankshaft. Hence, for example, the encoder may maintain positional information without power supplied thereto and may transmit to the controller input related to such information without rotation of the crankshaft (e.g., before the engine runs). It should be appreciated that the encoder may have any suitable resolution (e.g., 1 degree, ½ degree, ¼ degree, etc.), such that the controller receives information or signals related to the rotation of the crankshaft at every 1 degree, ½ degree, ¼ degree, etc. Alternatively or additionally, the controller may receive information or signals related every ¼ turn (e.g., every 90 degrees) of rotation of the crankshaft.

As described above, in at least one example, the engine may power a vehicle. Hence, in some instances, the controller may receive input from one or more sensors, which may be related to operating conditions of such vehicle. For example, such sensors (e.g., accelerometers, gyroscopes, etc.) may transmit to the controller input that may be related to movement of the vehicle, such as inclined or uphill movement, decline or downhill movement, turning, pivoting, etc.

In an embodiment, the sensors may include a Global Positioning System (GPS), which may provide global positioning coordinates for the vehicle powered by the engine. Hence, for instance, as described below in more detail, the controller may estimate the vehicle's movement at least in part based on the input received from the GPS. For example, the controller may correlate the global position coordinates and/or change thereof with position(s) on a map and may determine location of the vehicle on the map and movement of such vehicle relative to the map.

In one or more embodiments, the controller performs or executes an act 120 of determining amount of air to inject into one or more combustion chambers of the engine (e.g., into one or more cylinders of the engine). More specifically, for example, the controller may determine the amount of air to inject into the combustion chamber(s) based on the information or readings received from the sensors and/or based on the received input(s) related to the operating parameter(s) of the engine. In some instances, the controller may reference or refer to one or more algorithms, tables, databases, or combinations thereof to determine the amount of air to inject into the cylinders.

As mentioned above, the controller may correlate one or more inputs with operating parameter(s) of the engine. In particular, the controller may correlate inputs received from one or more users, sensors, etc., with the operating parameter(s) of the engine. For example, the controller may process input from a GPS to determine location of the vehicle that includes the engine and/or current and anticipate movement thereof (e.g., uphill, downhill, etc.); based on the location and current and/or anticipated movement of the vehicle, the controller may determine one or more operating parameter(s) of the engine. For instance, the controller may determine or calculate a combustion volume for the engine based on the current and/or anticipated movement of the vehicle and/or based on correlating current and/or anticipate load and/or power requirements (e.g., the controller may determine an increase in combustion volume to maintain the current RPM based on anticipate incline in the vehicle's route). In some examples, the controller may determine the combustion volume based on one or more additional or alternative parameters (e.g., local laws or ordinances related to allowable emissions). For instance, based on local laws or ordinances and based on the input from GPS, the controller may determine to reduce combustion volume (e.g., to less than internal volume of the cylinder, such that, for example, the combustion volume is at a pressure below atmospheric pressure).

In some embodiments, the controller refers to a table, chart, one or more formulas or algorithms, etc., which may correlate selected and/or predetermined amounts of fuel and air with revolutions per minute (RPM) produced at the crankshaft of the engine. It should be appreciated that such table may vary from one embodiment to the next and from one engine to another. In any event, however, at least in part based on such table(s) the controller may determine the amount of air to inject into the cylinders.

For instance, as mentioned above, the controller may receive input related to a requested operating parameter of the engine, such as RPM of the engine's crankshaft. Additionally or alternatively, as noted above, the controller may receive any number of suitable inputs, which may be converted to and/or correlated with operating parameter(s) of the engine. In an embodiment, based on such input, the controller may determine the amount of air to be injected into the cylinders. For example, the controller may choose or determine (e.g., based on user preferences) an optimal amount of air to minimize the amount of fuel for producing a requested RPM, thereby producing a lean combustion in the cylinder(s), as described below in more detail.

It should be appreciated that, because conventional engines may not precisely control the amount of air that enters the cylinder, typical conventional controls may adjust air intake mechanisms (e.g., throttle, turbo, etc.) to achieve a requested RPM. In at least one embodiment, precisely controlling the amount of air that is injected in the cylinder (e.g., by directly injecting a selected and/or predetermined amount of air into the cylinder) may facilitate producing selected and/or predetermined RPM based on such injection or series of injections. In other words, the controller may determine a specific amount of air to inject into the combustion chamber(s), such as cylinders, and produce a selected, predetermined, and/or requested RPM output, as compared with a conventional adjustments to air supply to the cylinders that are made based on the RPM (e.g., since a conventional controller may not have the information about the precise amount of air that enters the cylinder).

Likewise, as mentioned above, the controller may receive one or more inputs related to a requested volume for one or more cylinders. For example, the controller may receive a request to increase (e.g., by 100%, 200%, etc.) or decrease (e.g., 20%, 40%, 50%, etc.) the actual combustion volume of the cylinder. Based on such request, the controller may determine the amount or volume of air to inject into the cylinder(s). It should be appreciated that, in some instances, the determined amount of air to be injected may be less than the actual volume of the cylinder (e.g., at atmospheric pressure, the volume of air to be injected into the cylinder may be less than the volume of the cylinder).

In some examples, the controller may determine the amount of air to inject into each specific cylinder independently. For example, the controller may reduce the amount of air supplied into one or more cylinders, thereby reducing the combustion volume. Alternatively or additionally, the controller may determine to increase air supply into one or more cylinders (e.g., based on reduced supply of fuel) to produce lean combustion, such as for increased fuel economy. It should be appreciated that, in some instances, lean combustion may have higher combustion temperature, which may lead to increase engine temperature. The controller may determine to selectively produce lean combustion in one or more cylinders and periodically change cylinders that produce lean combustion (e.g., based on temperature input from one or more temperature sensors), in a manner that may avoid overheating the engine and/or damaging elements or components thereof.

In some instances, the controller may adjust the amount of air to be injected into the cylinders based on the input from one or more exhaust sensors. For instance, the controller may receive input that identifies the amount of oxygen in the exhaust gas. As such, the controller may adjust the previously determine amount of air based on the amount of oxygen present in the exhaust. Moreover, in some embodiments, the controller may adjust the algorithm (e.g., a formula), table values, etc., for making future determinations of the amount of air to be injected into the cylinder(s) in response to receiving the same or similar inputs, such as inputs from one or more of the sensor(s) and/or the same or similar operation inputs.

In an embodiment, the controller performs or executes an act 130 of operating one or more air injectors at least in part based on the determined amount of air. In particular, for instance, the controller may operate (directly or indirectly, such as by providing instructions for operating) the air injectors to inject air directly into the engine's cylinders (e.g., injecting air in at least substantially unimpeded manner). For example, the controller may open the air injectors in one, some, or all of the cylinders for a selected and/or predetermined period or amount of time, which would allow a selected, predetermined, and/or precise amount of air to enter the cylinder. As mentioned above, the controller may receive inputs that may be related to the air pressure at or near the air injectors. As such, for instance, the controller may determine the amount of time required to hold the air injector(s) open to allow a selected and/or predetermined amount of air to enter the cylinder (e.g., at least in part based on the input received from the air pressure sensor).

In any event, the controller may operate the air injector(s) to provide a predetermined and/or precise amount of air into the cylinder(s), thereby operating the engine at one or more selected and/or predetermined operating parameters (e.g., at selected and/or predetermined or requested RPM, temperature, fuel efficiency, etc.). Moreover, while the above acts are described in a particular order, it should be appreciated that such acts may be performed in any number of suitable sequences, which may vary from one embodiment to the next. For example, the controller may first receive input from one or more sensors (act 110) and subsequently receive one or more operation inputs related to operating parameter(s) of an engine (act 100).

Figure 10:
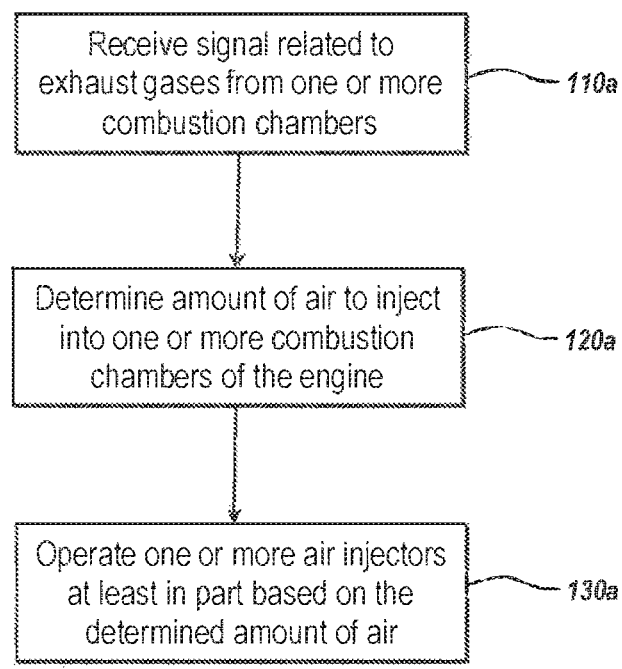
FIG. 10 is a flow chart of a method of controlling operation of an internal combustion engine according to another embodiment.

As mentioned above, the controller may receive information or signals from any number of suitable sensors or input sources, and such information or signals may be related any number of operating conditions or parameters of the engine. For instance, the controller may receive information or signals related to the exhaust exiting the combustion chambers of the engine. Furthermore, in some examples, the controller may operate the air injectors at least in part based on the information or signals received from the exhaust sensors. For example, FIG. 10 illustrates a flow chart of steps or acts that may be performed by a controller according to at least one embodiment.

More specifically, in an embodiment, the controller performs or executes an act 110*a* of receiving a signal related to exhaust gases from one or more combustion chambers. For example, the controller may receive information or signal from an exhaust sensor, which may indicate or may be related to the composition of the exhaust gases (e.g., the signal may be related to the amount of oxygen present in the exhaust). Additionally, in some embodiments, the controller executes or performs an act 120a of determining an amount of air to inject into one or more combustion chambers of the engine. In particular, such determination may be at least in part based on the signals or readings received from the exhaust sensor(s).

For example, based on the amount of residual Oxygen present in the exhaust, the controller may determine the amount of air to inject into the combustion chamber(s), such that the injected Oxygen is completely or substantially consumed during the combustion reaction. Hence, at least one embodiment includes an act 130a of operating one or more air injectors at least in part based on the amount of air determined by the controller. As noted above, for example, the controller may operate the air injectors by opening and/or maintaining open the air injectors for a selected and/or predetermined amount of time, such that a selected and/or predetermined amount of air enters the combustion chamber. Additionally or alternatively, the controller may provide information that includes the determined amount of air to be injected into the combustion chambers; the air injectors may be operated based on such information to inject a selected and/or predetermined amount of air into the combustion chamber(s) of the engine.

Figure 11:
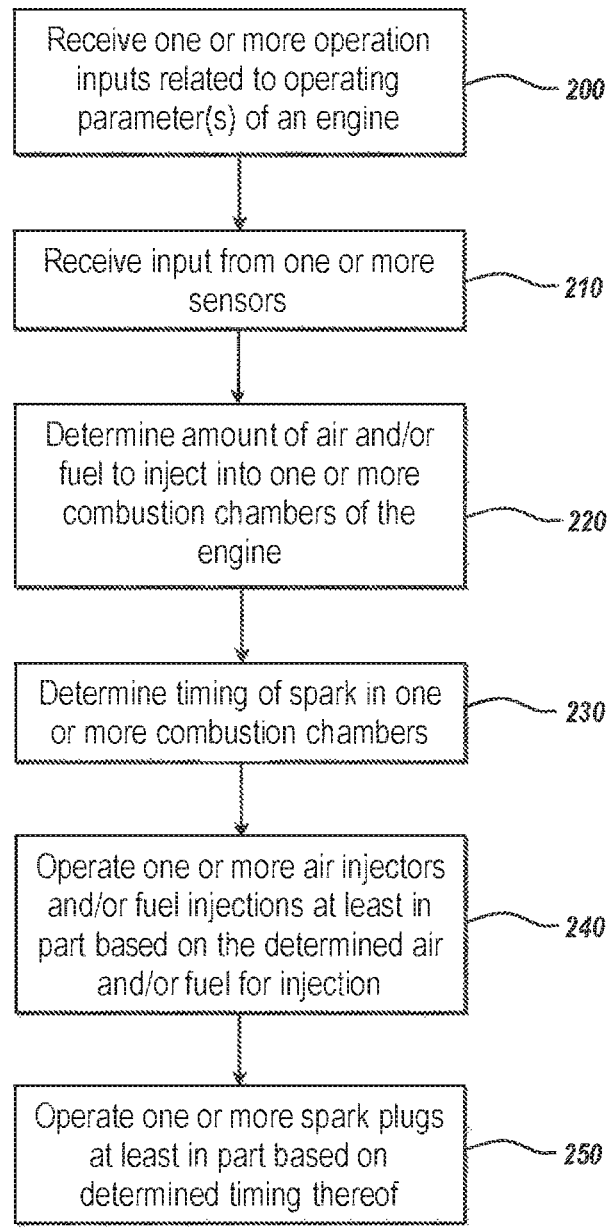
FIG. 11 is a flow chart of a method of controlling operation of an internal combustion engine according to yet another embodiment.

Also, in some embodiments, the controller may determine operating parameters for and/or may operate additional or alternative elements or components that may control operation of the engine. FIG. 11 illustrates a flow chart of steps or acts that may be performed by a controller according to at least one embodiment. Except as otherwise described herein, the acts described below may be similar to or the same as the acts described above in connection with FIGS. 9-10. In the illustrated example, the controller performs or executes an act 200 of receiving one or more operation inputs related to operating parameter(s) of an engine and act 210 of receiving input from one or more sensors, which may be similar to or the same as acts 100, 110 (FIG. 9).

In an embodiment, the controller performs or executes an act 220 of determining amount of air and/or fuel to inject into one or more combustion chambers (e.g., cylinders) of the engine, which may be based at least in part on the operation input(s) and/or on the input(s) from the sensor(s). For example, the controller may determine the amount of air to inject into the cylinder(s) in the same or similar manner as described above. Furthermore, the controller also may determine the amount of fuel to inject into the cylinder(s), thereby determining the air-fuel mixture to be injected into the cylinder(s).

It should be also appreciated that, in some embodiments, the air and fuel may mix outside of the combustion chamber(s) of the engine and may be injected together. Hence, for example, the controller may provide signals or instructions to one or more controlling elements (e.g., valves, injectors, etc.) that may dispense selected and/or predetermined amounts of air and/or fuel, which may mix together outside of the combustion chamber. Subsequently, the premixed air-fuel mixture may be supplied to (e.g., injected into) the combustion chamber(s) of the engine.

As mentioned above, the controller may receive input from the sensor(s) that may identify the type of fuel (e.g., composition of fuel) in the fuel cell (e.g., gas tank), fuel lines, near fuel injectors, or combinations thereof. Hence, the controller may determine the amount of fuel to be injected into the cylinder(s) at least in part based on the type of fuel that may be injected into the cylinder(s). In some embodiments, gasoline may be injected into the cylinders (e.g., oxidation reaction of gasoline may be represented as:

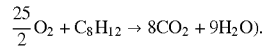

As such, for example, depending on the concentration of $O_2$ in the air, a stoichiometric air-gasoline mixture may be considered to burn at 14.7:1 (air-gasoline) ratio, at which the gasoline burns with no excess air or no oxygen being available after combustion. Hence, a lean mixture may have more air (e.g., ratio greater than 14.7:1), and a rich mixture may have more fuel (e.g., ratio less than 14.7:1). For instance, maximum power output may be produced at a rich mixture that may have air-gasoline of approximately 12.6:1, while best fuel economy may be at a lean air gasoline mixture, which may be at air-gasoline ratio of about 15.4:1 or greater. Under some operating conditions, the ratio may be ultra lean, such as about 65:1 and/or higher. It should be appreciated that ultra lean mixtures may combust at a relatively high temperature (e.g., higher than stoichiometric mixture). In some embodiments, the controller may determine a duration for operating the engine and/or one or more cylinders thereof at an elevated temperature that may result from the combustion of a lean or ultra lean mixture, such as to prevent damaging and/or breaking the engine and/or one or more cylinders thereof. Furthermore, the controller may determine and/or select injection of air and/or fuel to produce a suitable mixture to correspond with a load experienced by the engine and/or to correspond with a projected load.

For example, lean and/or ultra lean mixtures may be produced when a vehicle, such as a car, that is powered by the engine experiences a low load (e.g., at constant or reducing speeds, a car driving downhill, etc.). The controller may determine to produce a stoichiometric and/or rich mixtures when the load increases or is projected to increase (e.g., when a car is driving uphill or is projected to drive uphill).

In some instances, the controller may determine to inject a lean air-fuel mixture (e.g., to improve fuel economy). Moreover, for example, in the engine including combustion chambers formed by cylinders and pistons, the controller may selectively and/or continuously modify air-fuel mixtures injected into any cylinder. For example, the controller may produce a more lean combustion in one or some cylinders as compared with other cylinder(s). In some instances, the controller may produce lean combustion in one or some cylinders and stoichiometric or rich combustion in one or more other cylinders.

Stoichiometric combustion of at least some fuels (e.g., gasoline) may produce higher burn temperatures than rich combustion, and lean combustion may produce higher burn temperatures than stoichiometric combustion. Moreover, under some operating conditions, prolonged stoichiometric and/or lean combustion may damage or break one or more engine components and/or reduce useful life of the engine. In an embodiment, the controller may determine injection and/or combustion cycles that may maintain stoichiometric and/or lean combustion in one or more cylinders, while monitoring temperatures changes in the engine, and may modify combustion parameters in such combustion chambers (e.g., cylinders) to mitigate or eliminate temperature increase(s) that may be harmful to the engine. For instance, the controller may determine to terminate lean stoichiometric and/or lean combustion in one, some, or all of the cylinders and initiate rich combustion therein. Additionally or alternatively, the controller may determine to alternate between lean and rich combustion mixtures in one or multiple cylinders (e.g., some cylinders may operate with a lean combustion mixture, while others may operate with a rich combustion mixture).

Furthermore, as noted above, the controller may receive input or information about the orientation of the crankshaft and/or location(s) of the pistons in the cylinders (e.g., of a reciprocating engine). Under some operating conditions, the controller may determine to inject fuel and/or air into the cylinder(s) at various times and/or multiple locations of the piston. For example, in lieu of a single injection of a specific amount of fuel and/or air, the controller may direct fuel and/or air injectors to make multiple injections of fuel and/or air (e.g., which may generate the same power output at the crankshaft as the single injection of the same, lesser, or greater amount of fuel and/or air). In some instances, multiple injections of fuel and/or air may improve air-fuel mixing, combustion of the fuel, etc. Analogously, the controller may direct fuel and/or air injectors to make multiple injections of fuel and air (respectively) into a combustion chamber of a rotary engine (e.g., as the rotor thereof rotates).

Moreover, for a reciprocating engine, the controller may direct fuel and/or air injectors to inject fuel and/or air, respectively, during downward and/or upward movements of the piston. In some embodiments, the controller may direct fuel and/or air injectors to inject fuel and/or air during the down stroke of the piston (e.g., in a four stroke cycle, during the intake and/or during power stroke). For example, injecting air and/or fuel during the power stroke may improve ignition of the fuel and/or provide additional power. In one or more additional or alternative embodiments, the controller may direct fuel and/or air injectors to inject fuel and/or air during the exhaust stroke (e.g., in a four stroke cycle), which may aid in evacuating the exhaust gases out of the cylinder.

In some instances, the controller may determine to make multiple injections of air and fuel to produce stoichiometric and/or lean air-fuel mixtures in the combustion chamber(s) of the engine. For example, the controller may determine injection timings at least in part based on selected and/or predetermined orientations of the output shaft (e.g., orientation of the crankshaft of a reciprocating engine), selected and/or predetermined positions of the piston in the cylinder, combinations of the foregoing, etc. Moreover, the controller may determine to make one or more such air and fuel injections that may produce stoichiometric and/or lean mixtures, and to make one or more air and fuel injections that may produce rich mixtures (e.g., which may reduce or minimize temperature increase of the engine during the stoichiometric and/or lean combustion).

In some instances, the controller may determine to operate one or more cylinders of the engine at any even-numbered combustion cycle (e.g., two-, four- six-, etc.). For example, the controller may determine to inject air and fuel into one, some, or all cylinders on every down stroke of the piston, every second down stroke, every third down stroke, and so on. For instance, the controller may determine to operate some or all cylinders on a two-stroke cycle for a predetermine amount of time to meet power requirements requested in one or more inputs received by the controller and, under some conditions, may determine that subsequent to meeting such power requirements cylinders may be operated in four-stroke cycle.

In some embodiments, the controller may determine to turn off or shutdown one or some of the combustion chambers (e.g., one or some of the cylinders). For example, the controller may determine which cylinder(s) may be turned off to improve fuel efficiency while meeting the power output requirements. For example, the controller may determine to turn off fuel and/or air injection to one or more cylinders (e.g., to stop combusting fuel in such cylinders). Under some operating conditions, the controller may also determine to close and/or maintain closed exhaust valves of the turned off cylinders.

In some instances, a spark may be required to produce combustion of the air-fuel mixture in the cylinder(s). For example, an air-gasoline mixture may be ignited in the cylinder by a spark (e.g., from a fuel igniter, such as a spark plug). As such, in one or more embodiments, the controller performs or executes an act 230 of determining timing of spark in one or more combustion chambers (e.g., in the cylinders). For instance, for a reciprocating engine, the controller may determine to inject fuel and air at multiple times and/or locations during downward stroke of a piston. Similarly, the controller may determine one or more times for providing a spark in the cylinder, which may correspond with one or more times of fuel and/or air injections (e.g., at approximately the same time(s) as the fuel and air is injected; at a selected and/or predetermined amount of time after injection of air and/or fuel into the cylinder; at selected and/or predetermined locations of the piston and/or orientation of the crankshaft, which may be based on the input from the encoder; etc.). In any event, the controller may determine suitable times for providing a spark in the corresponding cylinder(s) to combust the air-fuel mixture therein.

As described above, generally, piston connector rods that may rotatably connect pistons to the crankshaft, and reciprocation of pistons in the corresponding cylinders may produce rotation of the crankshaft. As such, depending on angular position of the piston connector rod relative to the crankshaft, downward force on or movement of the piston may produce corresponding torque on and/or rotation of the crankshaft in a clockwise or counterclockwise direction. For instance, at top dead center (TDC), the connector rod may be parallel to center axis of the cylinder and perpendicular to the crankshaft (e.g., downward force on the piston may produce no rotation of the crankshaft). Analogously, when the piston is at a location that is before the TDC (BTDC) or after the TDC (ATDC), the connection point of the connector rod of the piston may be at a non-perpendicular angle relative to the rotation axis of the crankshaft (e.g., downward force onto the piston may produce corresponding clockwise or counterclockwise rotation of the crankshaft). For example, when the piston is BTDC, force applied to the piston may produce corresponding relative counterclockwise force and/or rotation of the crankshaft; when the piston is after TDC (ATDC), force applied to the piston may produce corresponding relative clockwise force and/or rotation of the crankshaft.

As noted above, the controller may receive input from an encoder, and such input may identify a relative orientation of the engine's crankshaft. Furthermore, in some instances, based on the relative radial orientation of the crankshaft, the controller may determine or correlate positions of the piston(s) in the cylinders (e.g., where each of the pistons is positioned relative to TDC). In some embodiments, the controller may start the engine without producing an initial rotation of the crankshaft and/or movement of the pistons (e.g., without a starter). For instance, the controller may determine or identify one or more cylinders that have pistons positioned at ATDC and may determine to inject air and/or fuel into such cylinders and to provide a spark into such cylinders (where suitable) for igniting air-fuel mixture (e.g., the controller may determine or identify the cylinders for providing air-fuel mixture and igniting such mixture to start the engine).

Furthermore, for the cylinders that have pistons at ATDC, the controller may determine the sequence of injecting air and/or fuel as well as for providing a spark to ignite the air-fuel mixture (e.g., at least partially in response to a received input requesting engine start). For instance, the controller may determine to start injection of fuel and/or air into the cylinder that has the piston at a selected and/or predetermined position or angle relative to the crankshaft (e.g., nearest to a selected and/or predetermined angle and/or after such selected and/or predetermined angle). For example, the controller may determine to start injection of fuel and air and/or may provide spark for igniting the air-fuel mixture in the cylinder that has a piston at least at ATDC 10 degrees and/or closest to 10 degrees relative to the crankshaft. The controller may also determine the amount of fuel and air to inject into such cylinders.

In some embodiments, the controller may determine or identify cylinders for injecting air and/or fuel as well as for igniting the air-fuel mixture to stop and/or reverse rotation of the crankshaft (e.g., at least partially in response to a received input indicating stoppage and/or reversal of the rotation of the crankshaft). As mentioned above, the controller may receive input that may identify locations of the pistons in the cylinders. For example, the controller may determine or identify cylinders that have pistons positioned at BTDC (e.g., on piston up stroke) and may determine the amount of air and/or fuel suitable for producing a combustion pressure to stop rotation of the crankshaft and/or reverse the rotation thereof. In other words, based on the operation of the engine and/or one or more received inputs (e.g., RPM of the crankshaft, load on the crankshaft, such as external load from a mechanism connected to the shaft, location(s) of the pistons in the cylinders at the time of received request to stop or reverse the rotation of the crankshaft, etc.), the controller may determine the amount of torque required or suitable to stop and/or reverse rotation. Moreover, in some examples, the controller may determine the amount of air and fuel to inject into one or more cylinders to produce the determined amount of torque for stopping and/or reversing rotation of the crankshaft.

As mentioned above, the engine may be included in any number of engine-powered vehicles (e.g., automobile, watercraft, aircraft, etc.). Hence, for instance, an operator of such vehicle may provide input or request at an interface for reversal of the rotation of the movement of the vehicle. The controller may subsequently receive the input indicating a request for reversal of rotation of the crankshaft of the engine, and may determine the amount of air and fuel to inject into the cylinder(s) to produce such reversal as well as may identify the specific or suitable cylinders for making such injections of air and fuel.

In at least one embodiment, the controller performs or executes an act 240 of operating one or more air injectors and/or fuel injections at least in part based on the determined air-fuel mixture. As mentioned above, the fuel and/or air may be directly injected into the selected and/or predetermined cylinders. In other words, the controller may determine or identify one or more cylinders for injecting air and fuel as well as igniting the air-fuel mixture in such cylinders; the controller may determine the amount of air and/or fuel to inject; the controller may determine the sequence (e.g., order of injections of air and/or fuel among the cylinders); the controller may determine combinations of the foregoing.

In some embodiments, the controller performs or executes an act 250 of operating one or more fuel igniters (e.g., spark plugs) at least in part based on determined timing of the spark (e.g., in act 230). For instance, for a reciprocating engine, the controller may determine the timing of providing the spark in one or more of the cylinders (e.g., based on the input from the encoder, which may be related to and/or may identify orientation of the crankshaft and/or corresponding positions of the pistons). Moreover, as described above, the encoder may have any suitable resolution (e.g., ½ degree or less, etc.); hence, in at least one embodiment, the controller may operate the fuel igniters without added or intentional delay between receiving the input from the encoder and operating the determined fuel igniter (e.g., only with the delay inherent in signal transmission from the controller to the fuel igniter and/or in computational operations of the controller).

Also, as described above, the controller may determine to inject air and/or fuel at multiple times and/or positions of the piston on the down stroke thereof. Moreover, the controller may operate the fuel and air injectors to inject air and fuel into the cylinder at such determined times and locations (of the pistons) as well as in the determined amounts. In at least one embodiment, the controller may operate the fuel igniters at multiple selected and/or predetermined times and/or locations of the piston in the cylinder, which may be related or correspond to the times of the controller's operation of the air and fuel injectors.

It should be appreciated that the above described acts 210-250 may be performed by the controller in any suitable order. Moreover, in some embodiments, one or more of the acts may be omitted and/or substituted. For instance, the engine may operate on any number of suitable fuels (e.g., diesel, hydrogen, propane, etc.) and, under some operating conditions, the controller may operate or control and engine without a spark (e.g., engine operating on diesel fuel). As such, in some examples, acts 230 and/or 250 may be omitted.

Figure 12:
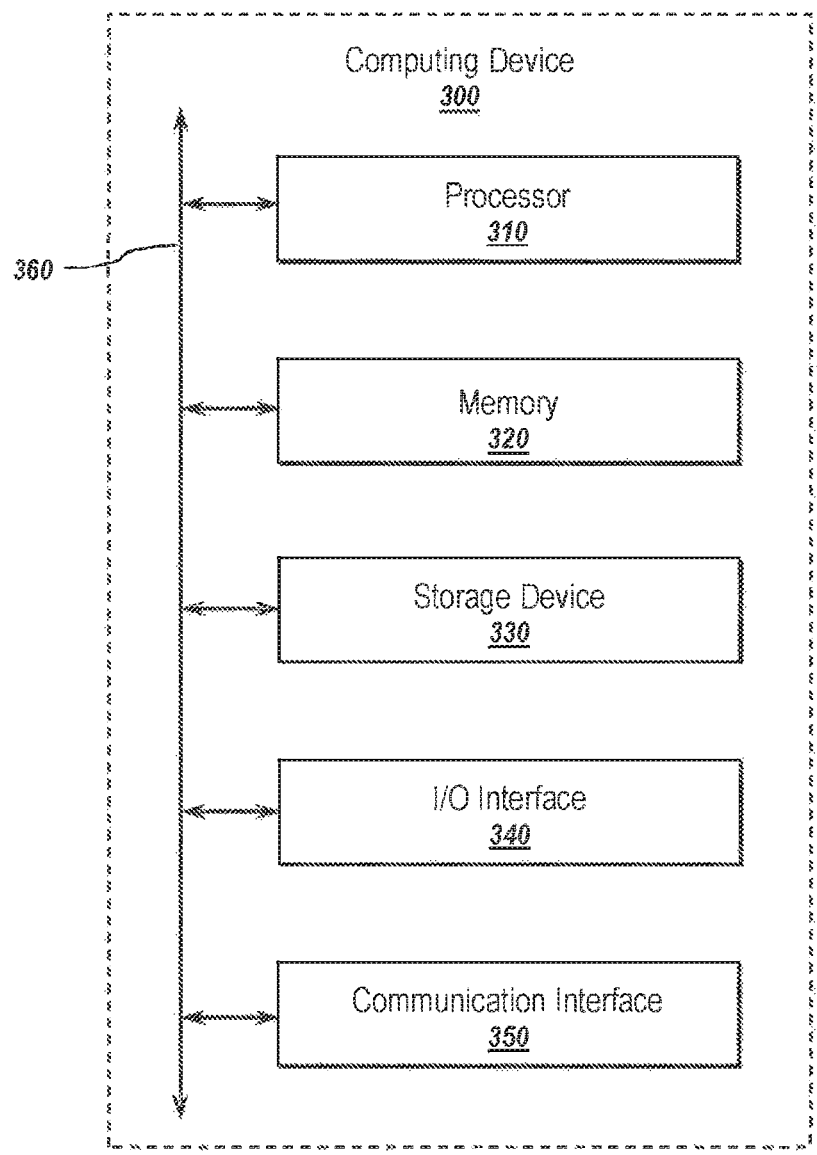
FIG. 12 is a block diagram of a controller according to an embodiment.

Generally, the controller described herein may include any number of suitable computing devices (e.g., engine control units (ECUs) that may be hardware and/or software programmed and/or operated). Moreover, the acts or steps described herein may be executed by a software instructions stored on the computing device (e.g., in the memory of the computing device) and/or by the hardware that is configured to execute such acts or steps. An example of a suitable computing device is illustrated in FIG. 12. More specifically, FIG. 12 is a block diagram of a computing device 300 according to an embodiment; the computing device 300 may be configured to perform one or more of the processes or acts described above.

For instance, the computing device 300 may include a computer program (e.g., software or hardware coded), which may direct or provide instructions to various components and/or elements of the computing device 300 to perform the acts described above. In an embodiment, the computing device may comprise a processor 310, memory 320, a storage device 330, an I/O interface 340, a communication interface 350, or combinations thereof. While FIG. 12 illustrates an exemplary computing device 300, the illustrated components are not intended to be limiting. Additional or alternative components may be used in other embodiments. Furthermore, in certain embodiments, a computing device 300 can include fewer components than those shown in FIG. 12.

In some embodiments, processor(s) 310 includes hardware for executing instructions, such as those making up a computer program. As an example and not by way of limitation, to execute instructions, processor(s) 310 may retrieve (or fetch) the instructions from an internal register, an internal cache, memory 320, or a storage device 330 and decode and execute them. In particular embodiments, processor(s) 310 may include one or more internal caches for data, instructions, or addresses. As an example and not by way of limitation, processor(s) 310 may include one or more instruction caches, one or more data caches, and one or more translation lookaside buffers (TLBs). Instructions in the instruction caches may be copies of instructions in memory 320 or storage 330.

The computing device 300 may include memory 320 coupled to the processor(s) 310. The memory 320 may be used for storing data, metadata, programs, or combinations thereof for execution by the processor(s). The memory 320 may include one or more of volatile and non-volatile memories, such as Random Access Memory ("RAM"), Read Only Memory ("ROM"), a solid state disk ("SSD"), Flash, Phase Change Memory ("PCM"), or other types of data storage. The memory 320 may be internal or distributed memory.

The computing device 300 may include a storage device 330 that may have storage for storing data and/or instructions. As an example and not by way of limitation, storage device 330 may comprise a non-transitory storage medium described above. The storage device 330 may include a hard disk drive (HDD), a floppy disk drive, flash memory, an optical disc, a magneto-optical disc, magnetic tape, or a Universal Serial Bus (USB) drive or a combination of two or more of these. Storage device 330 may include removable or non-removable (or fixed) media, where appropriate. Storage device 330 may be internal or external to the computing device 300. In some embodiments, storage device 330 is non-volatile, solid-state memory. Additionally or alternatively, the storage device 330 may include read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these.

The computing device 300 also may include one or more input or output ("I/O") interface(s) 340, which may be provided to allow a user to provide input to, receive output from, and otherwise transfer data to and from the computing device 300. For example, the I/O interface(s) 340 may be coupled to one or more sensors (described above (e.g., pressure sensors, temperature sensors, fuel sensors, etc.)) and/or to one or more input device (e.g., a throttle, a user interface, a mouse, keypad or a keyboard, a touch screen, camera, optical scanner, network interface, modem, other known I/O devices or combinations thereof). The touch screen may be activated with a stylus or a finger.

The I/O interface(s) 340 may include and/or may be coupled one or more devices for presenting output to a user, including, but not limited to, a graphics engine, a display (e.g., a display screen), one or more output drivers (e.g., display drivers), one or more audio speakers, and one or more audio drivers. In some embodiments, interface(s) 340 may be configured to provide graphical data to a display for presentation to a user. The graphical data may be representative of one or more graphical user interfaces and/or any other graphical content as may serve a particular implementation.

The computing device 300 may further include a communication interface 350. The communication interface may include hardware, software, or both. The communication interface 350 may provide one or more interfaces for communication (such as, for example, packet-based communication) between the computing device and one or more other computing devices 300 or one or more networks. As an example and not by way of limitation, communication interface 350 may include a network interface controller (NIC) or network adapter for communicating with an Ethernet or other wire-based network or a wireless NIC (WNIC) or wireless adapter for communicating with a wireless network, such as a WI-FI.

This disclosure contemplates any suitable network and any suitable communication interface 350. As an example and not by way of limitation, computing device 300 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computing system 300 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof. Computing device 300 may include any suitable communication interface 350 for any of these networks, where appropriate.

The computing device 300 may further include a bus 360. The bus 360 may comprise hardware, software, or both that couples components of computing device 300 to each other. As an example and not by way of limitation, bus 360 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

In some embodiments, a suitable engine control unit (ECU) may be used and/or programmed to control the elements and/or components of the engine and/or to perform the acts described herein. For example, the EMS-4, which is available from AEM Electronics, may be programmed and/or may store executable software code that may perform the acts described herein for a 4-cylinder engine. It should be appreciated that, while in some embodiments, the controller or a computing device may be special purpose computer, such as a suitable ECU, in additional or alternative embodiments, the controller or computing device may be a general purpose computer.

While the foregoing is directed to embodiments of the present invention, other and further embodiments of the invention may be devised without departing from the basic scope thereof, and the scope thereof is determined by the claims that follow.

What is claimed is:
1. A combustion engine, comprising:
one or more combustion chambers;
one or more conversion mechanisms each located in corresponding ones of the one or more combustion chambers, and each of the one or more conversion mechanisms being configured to convert a pressure increase in the combustion chamber into one or more of rotation of an output shaft or a linear movement of a linear output mechanism;

one or more oxidizer injectors operably connected to a supply of an oxidizer and configured to inject the oxidizer into corresponding ones of the one or more combustion chambers;

one or more fuel injectors configured to inject the fuel directly into the one or more combustion chambers;

one or more fuel lines operably connecting the one or more fuel injectors to a supply of fuel;

one or more fuel sensors configured to detect at least a type of the fuel, the one or more fuel sensors being secured to the one or more fuel lines to detect at least the type of the fuel, wherein the type of the fuel includes one or more of gasoline, diesel, liquefied natural gas, liquefied petroleum gas, or hydrogen;

one or more air lines in fluid communication with the one or more oxidizer injectors and with a source of compressed oxidizer;

an intake manifold connected to the one or more air lines, the intake manifold being sized and configured to distribute compressed oxidizer among the one or more air lines;

a compressor operably connected to the intake manifold, the compressor being configured to compress a gaseous oxidizer;

an air pressure regulator configured to regulate the pressure between the compressor and the intake manifold, wherein the air pressure regulator is automatically adjustable to a predetermined pressure during operation of the combustion engine;

a first air pressure sensor between the compressor and the air pressure regulator, the first air pressure sensor configured to detect output air pressure of the air compressor; and a second air pressure sensor between the air pressure regulator and the intake manifold, the second air pressure sensor configured to detect air pressure in the intake manifold.

2. The combustion engine of claim 1, further comprising a controller including a processor and a memory coupled to the processor and containing computer-executable instructions that, when executed by the processor cause the controller to perform acts of:

determining an amount of fuel to inject into the one or more combustion chambers at least in part based on the type of fuel detected by the one or more fuel sensors;

regulating operation of the compressor based at least in part on a reading or a signal from the first air pressure sensor; and automatically or dynamically adjusting the air pressure regulator during operating of the combustion engine based at least in part on a reading or a signal from the second air pressure sensor effective to produce at least one of a selected, a predetermined, or a suitable pressure in the intake manifold and the one or more air lines.

3. The combustion engine of claim 1, further comprising:

one more exhaust ports opening into corresponding ones of the one or more combustion chambers;

an exhaust manifold;

one or more exhaust lines in fluid communication with the exhaust manifold and with the corresponding ones of the one or more exhaust ports; and one or more exhaust valves operably connected to corresponding ones of the one or more exhaust lines, the one or more exhaust valves being operable to at least partially allow or prevent exhaust flow from the corresponding one or more combustion chambers.

4. The combustion engine of claim 1, wherein the conversion mechanism includes one or more pistons operably connected to the output shaft, and the one or more combustion chambers are defined by one or more cylinders and the one or more pistons moveably located in the corresponding ones of the one or more cylinders.

5. The combustion engine of claim 1, wherein:

the one or more oxidizer injectors include one or more air injectors operably connected to a supply of air and configured to inject the air into corresponding ones of the one or more combustion chambers; and the combustion engine includes no air intake valves for opening and closing air into the one or more combustion chambers other than the one or more air injectors.

6. A combustion engine, comprising:

an engine block including one or more cylinders therein;

a crankshaft rotatably secured to the engine block;

one or more pistons movably positioned in the one or more cylinders and operably connected to the crankshaft;

one or more oxidizer injection ports unobstructedly opening into corresponding ones of the one or more cylinders;

one or more oxidizer injectors positioned in corresponding ones of the one or more oxidizer injection ports and configured to inject an oxidizer into the corresponding one or more cylinders;

one or more fuel injectors configured to inject the fuel directly into the one or more combustion chambers;

one or more fuel lines operably connecting the one or more fuel injectors to a supply of fuel; and one or more fuel sensors configured to detect at least a type of the fuel, the one or more fuel sensors being secured to the one or more fuel lines to detect at least the type of the fuel, wherein the type of the fuel includes one or more of gasoline, diesel, liquefied natural gas, liquefied petroleum gas, or hydrogen;

one or more air lines in fluid communication with the one or more oxidizer injectors;

an intake manifold connected to the one or more air lines, the intake manifold being sized and configured to distribute compressed oxidizer among the one or more air lines;

a compressor operably connected to the intake manifold, the compressor being configured to compress a gaseous oxidizer;

an air pressure regulator configured to regulate the pressure between the compressor and the intake manifold, wherein the air pressure regulator is automatically adjustable to a predetermined pressure during operation of the combustion engine;

a first air pressure sensor between the compressor and the air pressure regulator, the first air pressure sensor configured to detect output air pressure of the air compressor; and a second air pressure sensor between the air pressure regulator and the intake manifold, the second air pressure sensor configured to detect air pressure in the intake manifold.

7. The combustion engine of claim 6, wherein the one or more oxidizer injectors are operable independently of one or more of rotation of the crankshaft or movement of the one or more pistons in the corresponding one or more cylinders.

8. The combustion engine of claim 6, further comprising:
one more exhaust ports opening into corresponding ones of the one or more cylinders;
an exhaust manifold;
one or more exhaust lines in fluid communication with the exhaust manifold and with the corresponding ones of the one or more exhaust ports; and
one or more exhaust valves operably connected to corresponding ones of the one or more exhaust lines, the one or more exhaust valves being operable independent of one or more of rotation of the crankshaft or movement of the one or more pistons, and operation of the one or more exhaust valves at least partially allows or prevents exhaust flow from the corresponding one or more cylinders.

9. The combustion engine of claim 6, further comprising:
one or more fuel injection ports unobstructedly opening into corresponding ones of the one or more cylinders, wherein the one or more fuel injectors are positioned in corresponding ones of the one or more fuel injection ports.

10. The combustion engine of claim 9, wherein the one or more fuel injectors are in fluid communication with a distribution rail sized and configured to distribute fuel among the one or more fuel injectors.

11. The combustion engine of claim 10, further comprising a fuel pressure regulator in fluid communication with the fuel rail and to a fuel tank and configured to control fuel pressure in the fuel rail.

12. The combustion engine of claim 11, wherein the supply of fuel includes a compressed gaseous fuel source, the one or more fuel injectors being in fluid communication with the compressed gaseous fuel source.

13. The combustion engine of claim 6, wherein:
the one or more oxidizer injectors include one or more air injectors operably connected to a supply of air and configured to inject the air into corresponding ones of the one or more cylinders; and
the combustion engine includes no air intake valves for opening and closing air into the one or more cylinders other than the one or more air injectors.

14. An internal combustion engine comprising fuel injectors for injecting fuel directly into one or more cylinders of the internal combustion engine, oxidizer injectors for injecting an oxidizer directly into the one or more cylinders of the internal combustion engine, one or more exhaust ports from corresponding ones of the one or more cylinders, one or more fuel sensors secured to one or more fuel lines of the internal combustion engine to detect at least a type of the fuel or the amount of ethanol in the fuel configured to detect at least the type of the fuel, each of the one or more exhaust ports leading to an exhaust valve which controls the flow of exhaust gases from the corresponding cylinder of the one or more cylinders, wherein the type of the fuel includes one or more of gasoline, diesel, liquefied natural gas, liquefied petroleum gas, or hydrogen.

15. The internal combustion engine of claim 14, wherein the one or more oxidizer injectors are in fluid communication with a source of a compressed oxidizer.

16. The internal combustion engine of claim 15, further comprising:
an engine block including the one or more cylinders therein;
a crankshaft rotatably secured to the engine block; and
one or more pistons movably positioned in the one or more cylinders and operably connected to the crankshaft;
wherein the one or more oxidizer injectors are operable independently of one or more of rotation of a crankshaft or movement of one or more pistons in the corresponding one or more cylinders.

17. The internal combustion engine of claim 14, wherein the oxidizer is air and the internal combustion engine includes no air intake valves for opening and closing air into the one or more combustion chambers other than the one or more air injectors.

* * * * *